US008778310B2

(12) United States Patent
Zhang et al.

(10) Patent No.: US 8,778,310 B2
(45) Date of Patent: Jul. 15, 2014

(54) FLUORESCENT CHLOROTOXIN CONJUGATE AND METHOD FOR INTRA-OPERATIVE VISUALIZATION OF CANCER

(75) Inventors: Miqin Zhang, Bothell, WA (US); Richard G. Ellenbogen, Seattle, WA (US); Raymond W. Sze, McLean, VA (US); Omid Veiseh, Kirkland, WA (US); James M. Olson, Seattle, WA (US); Mandana Veiseh, Emeryville, CA (US); Patrik Gabikian, Seattle, WA (US); S-Bahram Bahrami, Emeryville, CA (US)

(73) Assignees: University of Washington, Seattle, WA (US); Fred Hutchinson Cancer Research Center, Seattle, WA (US)

( * ) Notice: Subject to any disclaimer, the term of this patent is extended or adjusted under 35 U.S.C. 154(b) by 1234 days.

(21) Appl. No.: 11/897,721

(22) Filed: Aug. 31, 2007

(65) Prior Publication Data

US 2008/0279780 A1 Nov. 13, 2008

Related U.S. Application Data

(63) Continuation of application No. PCT/US2006/010170, filed on Mar. 20, 2006.

(60) Provisional application No. 60/674,280, filed on Apr. 22, 2005.

(51) Int. Cl.

| | |
|---|---|
| ***A61B 5/00*** | (2006.01) |
| ***A61B 8/00*** | (2006.01) |
| ***A61B 10/00*** | (2006.01) |
| ***A61K 49/00*** | (2006.01) |
| *A61K 38/16* | (2006.01) |
| *A61K 51/08* | (2006.01) |

(52) U.S. Cl.

CPC ............. *A61K 49/0032* (2013.01); *A61K 38/16* (2013.01); *A61K 49/0017* (2013.01); *A61K 49/005* (2013.01); *A61K 51/08* (2013.01)

USPC .......... 424/9.6; 424/1.11; 424/1.65; 424/1.69

(58) Field of Classification Search

CPC ..... A61K 51/088; A61K 51/08; A61K 51/00; A61K 51/02; A61K 51/04; A61K 51/06; A61K 51/065; A61K 2123/00; A61K 38/00; A61K 38/16; A61K 38/17; A61K 2121/00; A61K 49/005; A61K 49/0052; A61K 49/10; A61K 49/12; A61K 49/14; A61K 49/0032; A61K 49/0056; A61K 49/0021; A61K 49/00; A61K 49/001; A61K 49/0013; A61K 49/0017; A61K 49/0034; C07K 7/00; C07K 7/04; C07K 14/00

USPC ............. 424/1.11, 1.49, 1.65, 1.73, 1.81, 9.1, 424/9.6; 252/301.16, 625; 530/300, 324; 514/1, 1.1

See application file for complete search history.

(56) References Cited

U.S. PATENT DOCUMENTS

| | | | | |
|---|---|---|---|---|
| 5,905,027 | A * | 5/1999 | Ullrich et al. | 435/7.23 |
| 6,028,174 | A | 2/2000 | Ullrich et al. | |
| 6,130,101 | A | 10/2000 | Mao | |
| 6,319,891 | B1 | 11/2001 | Sontheimer et al. | |
| 6,429,187 | B1 | 8/2002 | Sontheimer et al. | |
| 6,514,481 | B1 | 2/2003 | Prasad | |
| 6,667,156 | B2 | 12/2003 | Lyons et al. | |
| 6,767,635 | B1 | 7/2004 | Bahr | |
| 6,870,029 | B2 | 3/2005 | Sontheimer et al. | |
| 6,972,326 | B2 | 12/2005 | Haugland | |
| 7,462,446 | B2 * | 12/2008 | Zhang et al. | 435/5 |
| 7,678,759 | B2 | 3/2010 | Sontheimer et al. | |
| 8,227,439 | B2 | 7/2012 | O'Neill et al. | |
| 8,470,607 | B2 | 6/2013 | Jacoby et al. | |
| 2002/0065216 | A1 | 5/2002 | Sontheimer et al. | |
| 2003/0201208 | A1 | 10/2003 | Koch | |
| 2004/0101822 | A1 | 5/2004 | Wiesner | |
| 2004/0102381 | A1 | 5/2004 | Ekwuribe et al. | |
| 2005/0142062 | A1 | 6/2005 | Sontheimer et al. | |
| 2006/0088899 | A1 | 4/2006 | Alvarez et al. | |
| 2006/0166892 | A1 | 7/2006 | Alvarez et al. | |
| 2007/0154965 | A1 | 7/2007 | Zhang et al. | |
| 2007/0237714 | A1 | 10/2007 | Alvarez | |
| 2007/0275902 | A1 | 11/2007 | Gonda et al. | |
| 2008/0153745 | A1 | 6/2008 | Alvarez et al. | |
| 2008/0153746 | A1 | 6/2008 | Alvarez et al. | |
| 2008/0279780 | A1 | 11/2008 | Zhang et al. | |

(Continued)

FOREIGN PATENT DOCUMENTS

| | | | |
|---|---|---|---|
| CN | 1924006 | A | 3/2007 |
| CN | 101003788 | A | 7/2007 |

(Continued)

OTHER PUBLICATIONS

Veiseh et al (Nano Letters, Apr. 30, 2005, vol. 5, No. 6, pp. 1003-1008).*

Berlier, J.E., et al., "Quantitative Comparison of Long-Wavelength Alexa Fluor Dyes to Cy Dyes: Fluorescence of the Dyes and Their Bioconjugates," The Journal of Histochemistry & Cytochemistry 51(12):1699-1712, 2003.

Butterworth, M.D., et al., "Preparation of Ultrafine Silica- and PEG-Coated Magnetite Particles," Colloids and Surfaces A: Physicochemistry Engineering Aspects 179:93 102, 2001.

(Continued)

*Primary Examiner* — D L Jones

(74) *Attorney, Agent, or Firm* — Wilson Sonsini Goodrich & Rosati

(57) ABSTRACT

A chlorotoxin conjugate detectable by fluorescence imaging that allows for intra-operative visualization of cancerous tissues, compositions that include the chlorotoxin conjugate, and methods for using the chlorotoxin conjugate.

14 Claims, 28 Drawing Sheets

(56) References Cited

U.S. PATENT DOCUMENTS

| | | | |
|---|---|---|---|
| 2009/0004105 | A1 | 1/2009 | Cheng et al. |
| 2009/0203598 | A1 | 8/2009 | McCarty et al. |
| 2009/0304592 | A1 | 12/2009 | O'Neill et al. |
| 2010/0098637 | A1 | 4/2010 | Orringer et al. |
| 2010/0210546 | A1 | 8/2010 | Alvarez et al. |
| 2010/0215575 | A1 | 8/2010 | O'Neill et al. |
| 2010/0215576 | A1 | 8/2010 | Sontheimer et al. |
| 2011/0027177 | A1 | 2/2011 | Jacoby et al. |
| 2011/0091380 | A1 | 4/2011 | Jacoby et al. |
| 2011/0311445 | A1 | 12/2011 | Alvarez et al. |
| 2012/0156131 | A1 | 6/2012 | Alvarez |
| 2012/0183544 | A1 | 7/2012 | Sontheimer et al. |
| 2013/0028836 | A1 | 1/2013 | Sentissi et al. |
| 2013/0045163 | A1 | 2/2013 | O'Neill et al. |
| 2013/0195760 | A1 | 8/2013 | Olson |

FOREIGN PATENT DOCUMENTS

| | | | |
|---|---|---|---|
| CN | 101270158 | A | 9/2008 |
| CN | 101381405 | A | 3/2009 |
| CN | 101824084 | A | 9/2010 |
| CN | 101921769 | A | 12/2010 |
| EP | 0155396 | A2 | 9/1985 |
| EP | 2182004 | A1 | 5/2010 |
| WO | WO 97/24619 | A1 | 7/1997 |
| WO | 00/62807 | A1 | 10/2000 |
| WO | WO 03/000203 | A2 | 1/2003 |
| WO | WO 03/101474 | A1 | 12/2003 |
| WO | WO 03/101475 | A1 | 12/2003 |
| WO | WO 2005/002604 | A1 | 1/2005 |
| WO | WO 2005/053611 | A2 | 6/2005 |
| WO | WO 2005/099774 | A2 | 10/2005 |
| WO | WO 2006/040574 | A2 | 4/2006 |
| WO | WO 2006/095164 | A1 | 9/2006 |
| WO | WO 2006/115633 | A2 | 11/2006 |
| WO | WO 2007/117467 | A2 | 10/2007 |
| WO | WO 2007/137163 | A2 | 11/2007 |
| WO | WO 2008/088422 | A2 | 7/2008 |
| WO | WO 2009/021136 | A1 | 2/2009 |
| WO | WO 2009/049184 | A2 | 4/2009 |
| WO | WO 2009/117018 | A1 | 9/2009 |
| WO | WO 2009/140599 | A1 | 11/2009 |
| WO | WO 2009/156456 | A1 | 12/2009 |
| WO | WO 2011/057295 | A2 | 5/2011 |
| WO | WO 2011/094671 | A2 | 8/2011 |
| WO | WO 2011/097533 | A1 | 8/2011 |
| WO | WO 2011/142858 | A2 | 11/2011 |
| WO | WO 2012/022742 | A1 | 2/2012 |

OTHER PUBLICATIONS

Citrin, D., et al., "In Vivo Tumor Imaging in Mice With Near-Infrared Labeled Endostatin," Molecular Cancer Therapeutics 3(4):481-488, 2004.

Deshane, J., et al., "Chlorotoxin Inhibits Glioma Cell Invasion Via Matrix Metalloproteinase-2," The Journal of Biological Chemistry 278(6):4135-4144, Feb. 7, 2003.

Kohler, N., et al., "A Bifunctional Poly(Ethylene Glycol) Silane Immobilized on Metallic Oxide Based Nanoparticles for Conjugation With Cell Targeting Agents," Journal of the American Chemical Society 126(23):7206 7211, 2004.

Soroceanu, L., et al., "Use of Chlorotoxin for Targeting of Primary Brain Tumors," Cancer Research 58:4871-4879, Nov. 1, 1998.

Sun, S., and H. Zeng, "Size Controlled Synthesis of Magnetite Nanoparticles," Journal of the American Chemical Society 124(28):8204 8205, 2002.

Veiseh, O., et al., "Optical and MRI Multifunctional Nanoprobe for Targeting Gliomas," Nano Letters 5(6):1003-1008, 2005.

Weissleder, R., and V. Ntziachristos, "Shedding Light Onto Live Molecular Targets," Nature Medicine 9 (1):123-128, Jan. 2003.

Zhang, Y., et al., "Surface Modification of Superparamagnetic Magnetite Nanoparticles and Their Intracellular Uptake," Biomaterials 23:1553 1561, 2002.

Gunn, J., et al., "Smart Superparamagnetic Imaging Probes for Brain Tumor Research," in D.B. Baer and C.T. Campbell (eds.), Joint Institute for Nanoscience Annual Report, 2004, Nov. 2005, pp. 3.65-3.66.

Jiang, T., et al., "Tumor Imaging by Means of Proteolytic Activation of Cell-Penetrating Peptides," Proceedings of the National Academy of Sciences USA (PNAS) 101(51):17867-17872, Dec. 2004.

Invitation Pursuant to Article 94(3) and Rule 71(1) EPC, mailed Mar. 1, 2010, in corresponding European Application No. 06 739 100.3, filed Mar. 20, 2006, 3 pages.

Akcan, et al. Chemical re-engineering of chlorotoxin improves bioconjugation properties for tumor imaging and targeted therapy. J Med Chem. Feb. 10, 2011;54(3):782-7. doi: 10.1021/jm101018r. Epub Jan. 6, 2011

Egleton, R.D. and Davis, T.P., Development of Neuropeptide Drugs that Cross the Blood-Brain Barrier, J. Am. Soc. Exp. NeuroTherapeutics 2:44-53 (2005).

European search report and search opinion dated Oct. 15, 2013 for EP Application No. 11780950.9.

Hockaday, D.C. et al., Imaging Glioma Extent with 131I-TM-601, J. Nuc. Med. 46(4): 580-586 (2005).

Huys, et al. Structure-function study of a chlorotoxin-chimer and its activity on Kv1.3 channels. J Chromatogr B Analyt Technol Biomed Life Sci. Apr. 15, 2004; 803(1):67-73.

International search report and written opinion dated Oct. 6, 2010 for PCT/US2006/010170.

International search report and written opinion dated Nov. 18, 2011 for PCT/US2011/023797.

Lee, M. J., et al., Rapid Pharmacokinetic and Biodistribution Studies Using Cholorotoxin-conjugated Iron oxide Nanoparticles: A Novel Non-Radioactive Method, PLoS One 5(3):e9536 1-8 (2010).

Milross, et al. Relationship of mitotic arrest and apoptosis to antitumor effect of paclitaxel. J Natl Cancer Inst. Sep. 18, 1996; 88(18):1308-14.

Tatikolov, A.S. And Costa, S.M.B., Complexation of polymethine dyes with human serum albumin: a spectroscopic study, Biophys. Chem. 107:33-49 (2004).

Tytgat, et al. Purification and partial characterization of a 'short' insectotoxin-like peptide from the venom of the scorpion Parabuthus schlechteri. FEBS Lett. Dec. 28, 1998; 441(3):387-91.

Veiseh, et al. Specific targeting of brain tumors with an optical/magnetic resonance imaging nanoprobe across the blood-brain barrier. Cancer Res. Aug. 1, 2009; 69(15):6200-7. doi: 10.1158/0008-5472.CAN-09-1157. Epub Jul. 28, 2009.

Veiseh, et al. Tumor paint: a chlorotoxin:Cy5.5 bioconjugate for intraoperative visualization of cancer foci. Cancer Res. Jul. 15, 2007; 67(14):6882-8.

Wishart, et al. 1H, 13C and 15N chemical shift referencing in biomolecular NMR. J.Biomol NMR. Sep. 1995; 6(2):135-40.

International search report and written opinion dated Apr. 8, 2014 for PCT/US2013/074215.

International search report and written opinion dated Apr. 22, 2014 for PCT/US2013/074218.

Shiue. Identification of candidate genes for drug discovery by differential display Drug Development Research. New York. 1997; 41:142-159.

* cited by examiner

| | MMP-2 | MMP-9 | |
|---|---|---|---|
| 9L - xenograft | + | - | |
| D283 - xenograft | + | - | |
| RH30 - xenograft | + | - | |
| Prostate Tumor | + | + | |
| Normal Prostate - Ant | - | - | |
| Normal Prostate - DVL | - | - | |
| Node Tumor | + | - | |
| SmoA1 Tumor | + | + | low levels |
| SmoA1 Tumor | + | + | low levels |
| SmoA1 Tumor | + | + | low levels |
| SmoA1 Tumor | + | + | low levels |
| Normal Cerebellum | - | - | |

FIGURE 11.

FLUORESCENT CHLOROTOXIN CONJUGATE AND METHOD FOR INTRA-OPERATIVE VISUALIZATION OF CANCER

CROSS-REFERENCES TO RELATED APPLICATIONS

This application is a continuation of PCT/US2006/010170, filed Mar. 20, 2006, which claims the benefit of U.S. Provisional Application No. 60/674,280, filed Apr. 22, 2005. Each application is incorporated herein by reference in its entirety.

STATEMENT OF GOVERNMENT LICENSE RIGHTS

This invention was made with government support under Grant Nos. N01 C037007-16, CA84296, and CA97186 awarded by the National Institutes of Health. The government has certain rights in the invention.

BACKGROUND OF THE INVENTION

For many types of cancer, the precision of surgical resection directly influences patient prognosis. Unfortunately, intra-operative identification of tumor margins or small foci of cancer cells remains imprecise or depends on surgical judgment. Thus, the extent of surgical resection is constrained by the requirement to avoid harming vital structures. Nowhere is this more problematic than in the brain, where greater than 80% of malignant cancers recur at the surgical margin. Despite advances in intra-operative monitoring and image guidance, post-operative scans sometimes reveal bulky residual tumor that may have been resected if the surgeon had improved tools to distinguish tumor tissue from normal brain. Recent advances in molecular biology, genomics and proteomics have yielded information about molecules that are expressed in malignant cells but not adjacent tissue. This information has the potential to fundamentally transform surgical oncology if used to specifically "paint" tumor cells with targeted molecular beacons.

Matrix metalloproteinase (MMP-2) is highly expressed in many common human malignancies including glioma, melanoma, sarcoma, breast cancer, colon adenocarcinoma, prostate cancer, neuroectodermal tumors, and ovarian cancer. MMP-2 and other MMP family members are believed to contribute to cancer invasion by proteolytic degrading adjacent non-neoplastic tissue.

Isolated from the scorpion *Leiurus quinquestriatus*, chlorotoxin (CTX) is a 36 amino acid peptide that was initially characterized as a ligand that blocked reconstituted chloride channels. It was thought that CTX inhibited glioma cell migration by blocking glioma-specific chloride channels, but this activity was subsequently attributed to CTX-mediated inhibition of MMP-2. Chlorotoxin binds preferentially to glioma cells compared to normal brain. A radiopharmaceutical bound to a synthetic chlorotoxin, $^{131}$I-TM-601, was recently approved for Phase I/II clinical trials for brain cancer therapy based on an acceptable safety profile in preclinical studies.

Cyanine compounds are molecular beacons that emit light in the near infrared (NIR) spectrum. Because light at this wavelength are minimally absorbed by water or hemoglobin, NIR beacons are well-suited for intra-operative imaging. Previous attempts to image brain tumors by NIR have focused on targeting the probe to inflammatory microglia around the tumor or utilizing probes that require proteolytic cleavage for activation. The former approach is problematic because the presence of microglia correlates poorly, if at all, with margins of many brain tumors. Furthermore, to reduce perioperative brain edema, patients are treated with dexamethasone which is a potent inhibitor of microglial activation.

Despite the advances in the development of probes for targeting and imaging brain tumors and in view of the factors noted above, there exists a need for a probe that does not require enzymatic cleavage and that allows for intra-operative visualization of cancerous tissues. The present invention seeks to fulfill this need and provides further related advantages.

SUMMARY OF THE INVENTION

In one aspect, the present invention provides a chlorotoxin conjugate detectable by fluorescence imaging that allows for intra-operative visualization of cancerous tissues.

In one embodiment, the chlorotoxin conjugate of the invention includes one or more red or near infrared emitting fluorescent moieties covalently coupled to a chlorotoxin.

In another embodiment, the invention provides a fluorescent chlorotoxin conjugate having a prolonged half-life in vivo. The fluorescent chlorotoxin conjugate includes one or more fluorescent moieties covalently coupled to a chlorotoxin. In one embodiment, the conjugate has a sufficiently long half-life to enable biophotonic imaging of cancer from about 4 to about 14 days after administration of the chlorotoxin conjugate.

In another aspect of the invention, compositions that include the chlorotoxin conjugate are provided. The composition is suitable for administration to a human and includes pharmaceutically acceptable carrier. The composition includes a pharmacologically effective amount of a chlorotoxin conjugate.

In another aspect, the invention provides methods for using the chlorotoxin conjugate to detect tissues of interest.

In one embodiment, a method for differentiating foci of cancers that express chlorotoxin binding sites from non-neoplastic tissue is provided. The method includes the steps of:

(a) contacting a tissue of interest with a chlorotoxin conjugate having affinity and specificity for cells that express chlorotoxin binding sites, wherein the chlorotoxin conjugate comprises one or more red or near infrared emitting fluorescent moieties covalently coupled to a chlorotoxin; and (b) measuring the level of binding of the chlorotoxin conjugate, wherein an elevated level of binding, relative to normal tissue, is indicative that the tissue is neoplastic.

In one embodiment, a method for detecting cancers that express chlorotoxin binding sites is provided. The method includes the steps of:

(a) contacting a tissue of interest with a chlorotoxin conjugate having affinity and specificity for cells that express chlorotoxin binding sites, wherein the chlorotoxin conjugate comprises one or more red or near infrared emitting fluorescent moieties covalently coupled to a chlorotoxin; and (b) measuring the level of binding of the chlorotoxin conjugate, wherein an elevated level of binding, relative to normal tissue, is indicative that the tissue is neoplastic.

In one embodiment, a method for detecting cells expressing matrix metalloproteinase (MMP-2) protein complex is provided. The method includes the steps of:

(a) contacting a tissue of interest with a chlorotoxin conjugate having affinity and specificity for matrix metalloproteinase (MMP-2) protein complex, wherein the chlorotoxin conjugate comprises one or more red or near infrared emitting fluorescent moieties covalently coupled to a chlorotoxin; and (b) measuring the level of binding of the chlorotoxin conjugate, wherein an elevated level of binding, relative to normal tissue, is indicative of the presence of a tumor expressing matrix metalloproteinase (MMP-2) protein complex.

In one embodiment, a method for determining the location of cancer cells that express chlorotoxin binding sites in a patient intra-operatively is provided. The method includes the steps of:

(a) administering a pharmaceutical composition to a patient, wherein the pharmaceutical composition comprises a pharmaceutically acceptable carrier and an amount of a chlorotoxin conjugate sufficient to image cancer cells that express chlorotoxin binding sites in vivo, wherein the chlorotoxin conjugate comprises one or more red or near infrared emitting fluorescent moieties covalently coupled to a chlorotoxin;

(b) measuring the level of binding of the chlorotoxin conjugate by fluorescence imaging to determine the location of cancer cells that express chlorotoxin binding sites, wherein an elevated level of binding, relative to normal tissue, is indicative of the presence of cancer cells that express chlorotoxin binding sites; and (c) surgically removing from the patient at least some cells that express chlorotoxin binding sites located by fluorescence imaging.

In another aspect, the invention provides methods for using the chlorotoxin conjugate to treat tissues of interest.

In one embodiment, the invention provides a method for treating a cancer that expresses chlorotoxin binding sites in a patient, comprising administering to a patient in need thereof an effective amount of a pharmaceutical composition comprising the chlorotoxin conjugate of the invention and a pharmaceutically acceptable carrier.

In one embodiment, the invention provides a method for treating a cancer that expresses chlorotoxin binding sites, comprising administering to a patient in need thereof an effective amount of a pharmaceutical composition comprising the chlorotoxin conjugate of the invention and a pharmaceutically acceptable carrier.

In one embodiment, the invention provides a method for treating a tumor expressing matrix metalloproteinase (MMP-2) protein complex, comprising administering to a patient in need thereof an effective amount of a pharmaceutical composition comprising the chlorotoxin conjugate of the invention and a pharmaceutically acceptable carrier.

In one embodiment, the invention provides a method for inhibiting invasive activity of cells that express chlorotoxin binding sites, comprising administering to cells that express chlorotoxin binding sites an effective amount of a pharmaceutical composition comprising the chlorotoxin conjugate of the invention and a pharmaceutically acceptable carrier.

Methods for making the chlorotoxin conjugates are also provided.

DESCRIPTION OF THE DRAWINGS

The patent or application file contains at least one drawing executed in color. Copies of this patent or patent application publication with color drawings will be provided by the Office upon request and payment of the necessary fee.

The foregoing aspects and many of the attendant advantages of this invention will become more readily appreciated as the same become better understood by reference to the following detailed description, when taken in conjunction with the accompanying drawings, wherein:

FIGS. 2A and 2B show a representative chlorotoxin conjugate of the invention (CTX:Cy5.5) emits signal from every 9L glioma cell in culture (FIG. 2A), but fails to bind fibroblasts (FIG. 2B); FIG. 2C illustrates specific binding of CTX:Cy5.5 is detected in glioma xenograft, but not otherwise normal organs of a mouse bearing a 9L glioma xenograft 32 days after systemic administration of 0.2 ml of 10 μM conjugate; FIG. 2D illustrates biophotonic images of brains from stereotaxically injected 9L glioma (top), sham surgery control (middle), and no surgery control (bottom) animals taken 1.5 days after administration of 0.2 ml of 10 μM conjugate; FIG. 2E illustrates H&E stained sections from thalamus with 9L glioma invasion (top) and thalamus of uninjected control (bottom), these images correspond to the designated regions in FIG. 2D; and FIG. 2F illustrates the inhibition of CTX:Cy5.5 binding by the MMP-2 blocker, 1,10-phenanthroline (left top and left bottom) compared to binding in control mice that did not receive 1,10-phenanthroline (right top and bottom);

FIGS. 3A-3D are images illustrating detection of autochthonous medulloblastoma in genetically engineered mice; FIG. 3A illustrates biophotonic images of tumor-free wild type mouse (left) and ND2:SmoA1 mouse (right), mice were injected with 0.2 ml of 10 μM of a representative chlorotoxin conjugate of the invention (CTX:Cy5.5) 1.5 days prior to imaging; FIG. 3B illustrates images of brains from the same mice following necropsy; FIG. 3C illustrates histologic confirmation of medulloblastoma (right) compared to normal cerebellum (left); and FIG. 3D illustrates confocal microscopy images from the same brains shown in FIG. 3B demonstrating near absence of Cy5.5 signal in control (left) and high signal in medulloblastoma (right);

FIG. 4A illustrates fluorescent images of Cy5.5 signal (red) in foci of prostate cancer (CAP) adjacent to normal prostate (NP, green autofluorescence) in human surgical specimens (1st and 3rd panels), the 5th panel is normal prostate, showing no Cy5.5 signal, corresponding H&E stained adjacent sections are shown to the right of each NIR image; FIG. 4B illustrates biophotonic images of prostate and other organs from TRAMP mouse (top panel) and wild type control (bottom panel) showing specific signal in TRAMP prostate (CAP) and lung (red arrow), images were obtained 5.5 days after injection of 0.1 ml of 10 μM conjugate, top row organs: brain, heart, kidney, liver, lung, spleen, and lower row: prostate; FIG. 4C illustrates confocal microscopy sections from the same prostate samples shown in FIG. 4B, high CTX:Cy5.5 binding was present in nearly every cell of the prostate cancer (top left) and was minimal in normal prostate (bottom left), H&E stained adjacent sections (center) show lung metastases in the TRAMP mouse lung (upper right) that is bright in FIG. 4B and normal lung from the control mouse (lower right); and FIG. 4D illustrates intra-operative images of control (left) and TRAMP (right) mouse abdomen following removal of intestine, prostate, and liver, multiple lymph nodes (N) were positive by biophotonic imaging and histology, a 1.5 mm diameter tissue nodule that was very bright on imaging revealed three small foci of prostate cancer cells in lymph channels surrounded by fat and reactive tissue (L), lower amounts of signal were detected in fat (F) and testes (T); FIG. 4E illustrates hematoxylin and eosin stained section showing a small focus of cancer cells in a lymph channel (labeled L in FIG. 4D) and cancer-containing lymph node;

FIG. 5A is an H&E stained section of adenocarcinoma shown in FIG. 5B; FIG. 5B illustrates biophotonic images of adenocarcinoma (left) and adenoma (right) showing clear delineation from normal intestine; FIG. 5C illustrates histologic confirmation of adenoma shown in FIG. 5B; FIG. 5D illustrates NIR images of RH30 rhabdomyosarcoma xenograft from mouse that was not injected with CTX:Cy5.5 (top) and a mouse that received 0.2 ml of 10 μM CTX:Cy5.5 1.5 days prior to imaging; FIG. 5E illustrates confocal images of the corresponding tumors from mice that were uninjected (left) and injected (right); and FIG. 5F is a histopathologic analysis of rhabdomyosarcoma xenograft;

FIG. 7A shows no tumor-specific signal is seen with CTX:fluorescein in mice bearing 9L gliomas within the first hour after imaging; FIG. 7B illustrates a mouse on the left was injected with CTX:fluorescein directly into the tumor to demonstrate that the conjugate was emitting and being detected properly; FIG. 7C illustrates a mouse with 9L glioma imaged within 1 hour after injection of CTX:ALEXA-680 showing signal in tumor; FIG. 7D is an image 24 hours after injection, excellent signal is observed from CTX:Cy5.5 in tumor compared to opposite non-neoplastic flank (the signal above the tumor is from kidney excretion of bioconjugate), a weaker signal from tumor is seen in ALEXA-680 treated mouse #2, but not #1, reinjection of mouse #1 resulted in rapid clearance of conjugate from non-neoplastic and tumor tissue showing that the conjugate is rapidly cleared in this mouse; and FIG. 7E are images of the same animals as panel FIG. 7D, signal remains in CTX:Cy5.5-injected mouse, but no tumor-specific signal is observed in CTX:ALEXA-680-injected mice; taken together, the data indicate that no tumor specific signal is seen with CTX:Fluorescein and that a weak signal from CTX:ALEXA-680 is fleeting compared to CTX:Cy5.5 indicating that the CTX:Cy5.5 conjugate is superior to other tested conjugates in terms of specific distribution to tumor and overall duration of tumor signal;

FIG. 8A shows MCF-7 breast cancer cell stained with an antibody against MMP-2 (green) and CTX:Cy5.5 (red) shows minimal MMP-2 and minimal CTX:Cy5.5 binding, the nucleus is stained with DAPI to assist with cell localization in the image; and FIG. 8B shows MCF-7 breast cancer cell following transfection with a plasmid that encodes MMP-2, staining with the antibody against MMP-2 shows that the transfection resulted in MMP-2 expression in this cell (green), CTX:Cy5.5 staining (red) is much higher than in any of the control cells, yellow shows cell regions in which MMP-2 signal and CTX:Cy5.5 signal are overlapping, no DAPI stain is shown to optimize visualization of MMP-2 and CTX:Cy5.5 binding;

FIG. 9A is an image of a HPTLC plate was developed in chloroform:methanol:water (65:25:4) and lipids were visualized with the lipophilic dye, primulin; and FIG. 9B is an image pf a HPTLC overlay of lipids with 1 uM CTX:Cy5.5; abbreviations: PS, phosphatidylserine; PI, phosphatidylinositol: PG, phosphatidylglycerol; PE, phosphatidylethanolamine; PIP2, phosphatidylinositol 4,5-bisphosphate; PC, phosphatidylcholine; SM, sphingomyelin;

FIG. 10A, hematoxylin and eosin (H&E) stained section of glioma; FIG. 10B, CTX:Cy5.5 staining of same glioma; FIG. 10C, Cy5.5 alone does not stain glioma; FIG. 10D, H&E stained section of normal brain from same patient; and FIG. 10E, CTX:Cy5.5 does not stain normal brain;

FIG. 11 illustrates MMP-2 and MMP-9 activity in mouse tumors and normal tissue; gelatinase assays were conducted to evaluate MMP-2 expression in the tissues listed above; MMP-2 activity was detected in all cancer foci that were detected by CTX:Cy5.5, but not corresponding non-neoplastic tissue; and MMP-9 activity was detected in mouse medulloblastoma tumors (SmoA1) and prostate tumor, but not xenograft tumors or normal tissues;

FIG. 13A shows MCF-7 cells incubated with CTX:Cy5.5 fail to emit in the near infrared (Cy5.5) spectrum (red), nuclei are stained blue with DAPI; FIG. 13B shows a sister plate of MCF-7 cells incubated with the same amount of CTX:Cy5.5 as in FIG. 13A, except this CTX:Cy5.5 was transferred in media after 24 hour exposure to 9L glioma cells (CTX:Cy5.5 stains MCF-7 cells under this condition); FIG. 13C shows a sister plate of MCF-7 cells stained with CTX:Cy5.5 using conditioned media from U87 cells; FIG. 13D shows CTX:Cy5.5 staining of HeLa cells, no red staining indicates absence of CTX:Cy5.5 signal; FIG. 13E shows a sister plate of HeLa cells stained with CTX:Cy5.5 in conditioned media from 9L cells; and FIG. 13F shows a sister plate of HeLa cells stained with CTX:Cy5.5 in conditioned media from U87 cells.

DETAILED DESCRIPTION OF THE INVENTION

Figure 1A:
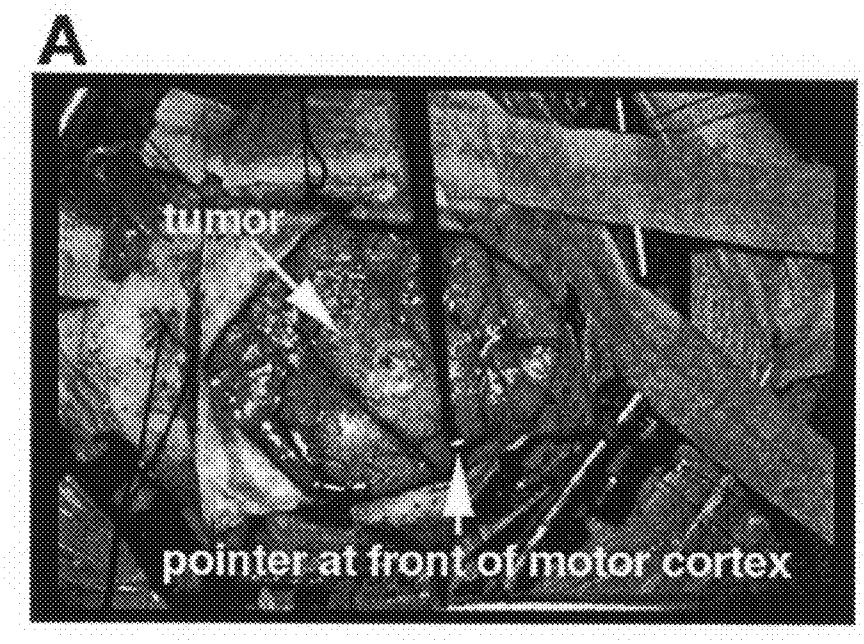
FIG. 1A is an intra-operative photograph illustrating the clinical problem, intrinsic brain tumor tissue is often indistinguishable from normal brain tissue.
Figure 1B:
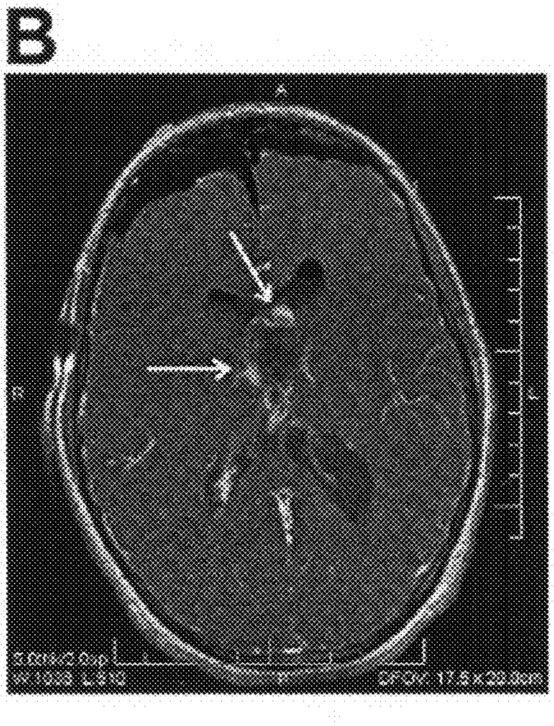
FIG. 1B is a post-operative magnetic resonance (MR) image showing gross residual disease at sites where the glioma was intra-operatively indistinguishable from adjacent brain despite intra-operative electrophysiologic monitoring.

The present invention provides a chlorotoxin conjugate detectable by fluorescence imaging that allows for intra-operative visualization of cancerous tissues, compositions that include the chlorotoxin conjugate, and methods for using the chlorotoxin conjugate.

In one aspect, the present invention provides a chlorotoxin conjugate detectable by fluorescence imaging that allows for intra-operative visualization of cancerous tissues.

The chlorotoxin is a targeting agent that directs the conjugate to a tissue of interest. In one embodiment, the chlorotoxin conjugate of the invention includes one or more red or near infrared emitting fluorescent moieties covalently coupled to a chlorotoxin.

The chlorotoxin may be native chlorotoxin, synthetic chlorotoxin, or recombinant chlorotoxin. Chlorotoxin fragments and variants having chlorotoxin binding activity (e.g., specificity and affinity to cancerous tissues) may also be used.

As used herein, the term "red or near infrared emitting fluorescent moiety" refers to a fluorescent moiety having a fluorescence emission maximum greater than about 600 nm. Fluorescent chlorotoxin conjugates having shorter wavelength (e.g., from about 500 to about 600 nm) emitting fluorescent moieties are useful in histochemical imaging. These conjugates may be useful less for in vivo imaging in humans and animals where longer wavelength (e.g., greater than about 600 nm) emitting fluorescent moieties are preferred.

In certain embodiments of the chlorotoxin conjugate, the fluorescent moieties are derived from fluorescent compounds characterized by emission wavelength maxima greater than about 600 nm to avoid autofluorescence, emission that travels through millimeters to one centimeter of tissue/blood/fluids, emission that is not absorbed by hemoglobin, other blood components, or proteins in human or animal tissue.

The fluorescent moiety is covalently coupled to the chlorotoxin to allow for the visualization of the conjugate by fluorescence imaging. The fluorescent moiety is derived from a fluorescent compound. Suitable fluorescent compounds are those that can be covalently coupled to a chlorotoxin without substantially adversely affecting the targeting and binding function of the chlorotoxin conjugate. Similarly, suitable fluorescent compounds retain their fluorescent properties after conjugation to the chlorotoxin.

In one embodiment, the fluorescent moiety is a cyanine moiety. Cyanine compounds are characterized by their relative high extinction coefficients and favorable fluorescence quantum yields. The fluorescence emission wavelength maximum for a cyanine compound varies as a function of the cyanine structure. Depending on the particular cyanine compound, the fluorescence emission wavelength maxima can vary from the green (about 490 nm) to the near infrared (about 740 nm). In the practice of the methods of the invention, cyanine compounds having fluorescence emission maxima in the far red (about 650 nm) to the near infrared (about 750 nm) are preferred. At these emission wavelengths, background fluorescence from the local environment is minimal and tissues of interest are relatively transparent. Because of the relative transparency of the tissues of interest at these wavelengths, excitation and fluorescence emission visualization is maximized and relatively greater amounts of tissue targeted by the conjugate of the invention can be observed compared to other conjugates utilizing fluorescent compounds having emission at shorter wavelengths (less than 600 nm).

Suitable cyanines include the CYDYE fluors commercially available from GE Healthcare under the designation Cy2 (506 nm); Cy2 (506 nm); Cy3 (570 nm); Cy3B (572 nm); Cy3.5 (596 nm); Cy5 (670 nm); Cy5.5 (675 nm); and Cy7 (694 nm) (emission maxima in parentheses). In one embodiment, the cyanine compound is Cy5.5. The preparation of a representative cyanine-chlorotoxin conjugate is described in Example 1.

In one embodiment, the fluorescent moiety is a sulfonated xanthene moiety. Sulfonated xanthene compounds suitable for use in the practice of the invention are described in U.S. Pat. No. 6,130,101, expressly incorporated herein by reference in its entirety, and commercially available under the designation ALEXA FLUOR from Molecular Probes, Inc., Eugene, Oreg. ALEXA FLUOR is the designation for a family of fluorophores that are characterized by their relative high extinction coefficients and favorable fluorescence quantum yields. The fluorescence emission wavelength maximum for a sulfonated xanthene compound varies as a function of the compound's structure. Depending on the particular sulfonated xanthene compound, the fluorescence emission wavelength maxima can vary from the green (about 450 nm) to the near infrared (about 780 nm). In the practice of the methods of the invention, ALEXA FLUOR compounds having fluorescence emission maxima in the far red (about 650 nm) to the near infrared (about 750 nm) are preferred.

Suitable sulfonated xanthene compounds include ALEXA FLUORS, such as ALEXA FLUOR 350 (442 nm), ALEXA FLUOR 405 (421 nm), ALEXA FLUOR 488 (539 nm), ALEXA FLUOR 500 (525 nm), ALEXA FLUOR 514 (540 nm), ALEXA FLUOR 532 (554 nm), ALEXA FLUOR 546 (575 nm), ALEXA FLUOR 555 (565 nm), ALEXA FLUOR 568 (603 nm), ALEXA FLUOR 594 (617 nm), ALEXA FLUOR 610 (628 nm), ALEXA FLUOR 633 (647 nm), ALEXA FLUOR 635 (645 nm), ALEXA FLUOR 647 (668 nm), ALEXA FLUOR 660 (690 nm), ALEXA FLUOR 680 (702 nm), ALEXA FLUOR 700 (719 nm), and ALEXA FLUOR 750 (779 nm) (emission maxima in parentheses). In one embodiment, the sulfonated xanthene is ALEXA FLUOR 680. Representative sulfonated xanthene-chlorotoxin conjugates can be prepared in manner analogous to that described for cyanine conjugation in Example 1 and as further described in *The Handbook—A Guide to Fluorescent Probes and Labeling Technologies*, Richard P. Haugland (Molecular Probes, Inc., a subsidiary of Invitrogen Corp.).

Suitable fluorescent compounds include a functional group that renders the compound chemically reactive toward the chlorotoxin. Suitable functional groups include the N-hydroxysuccinimide (NHS) group for covalent coupling to amine groups, the maleimide group for covalent coupling to thiol groups, and the hydrazide group for covalent coupling to aldehyde groups. Preferably, the fluorescent compound useful in preparing the conjugate of the invention includes a single reactive functional group (e.g., mono-NHS ester). It will be appreciated that other conjugating chemistries are suitable for making the chlorotoxin conjugate of the present invention.

Suitable conjugates of the invention include from about 1 to about 3 fluorescent moieties/chlorotoxin. In one embodiment, the conjugate include about 1 fluorescent moiety.

The preparation of a representative chlorotoxin conjugate of the invention is described in Example 1. In vitro imaging using a representative chlorotoxin conjugate of the invention is described in Example 2. In vivo imaging using a representative chlorotoxin conjugate of the invention is described in Example 3. The involvement of MMP-2 in chlorotoxin binding is described in Example 4.

In another aspect, the invention provides a fluorescent chlorotoxin conjugate having a prolonged half-life in vivo. The fluorescent chlorotoxin conjugate includes one or more fluorescent moieties covalently coupled to a chlorotoxin. In one embodiment, the conjugate has a sufficiently long half-life to enable biophotonic imaging of cancer from about 4 to about 14 days after administration of the chlorotoxin conjugate.

In another aspect of the invention, compositions that include the chlorotoxin conjugate are provided. The composition is suitable for administration to a human and animal subjects and includes pharmaceutically acceptable carrier. The composition includes a pharmacologically effective amount of a chlorotoxin conjugate. An effective amount can be routinely determined by established procedures. An effective amount is an amount sufficient to occupy chlorotoxin binding sites in cancer cells, but low enough to minimize non-specific binding to non-neoplastic tissues. An effective amount optimizes signal-to-noise ratio for intra-operative imaging.

In other aspects, the invention provides methods for using the chlorotoxin conjugate to detect and treat tissues of interest.

The invention provides methods for detecting a tissue using the chlorotoxin conjugates. The chlorotoxin conjugates of the invention target and are bound by chlorotoxin binding sites. It will be appreciated that chlorotoxin binding sites may take two forms: sites that bind chlorotoxin and sites that bind the chlorotoxin conjugates of the invention. It will be appreciated that chlorotoxin binding sites may be distinct from chlorotoxin conjugate binding sites.

In one embodiment, a method for differentiating foci of cancers that express chlorotoxin binding sites from non-neoplastic tissue is provided. The method includes the steps of:

(a) contacting a tissue of interest with a chlorotoxin conjugate having affinity and specificity for cells that express chlorotoxin binding sites, wherein the chlorotoxin conjugate comprises one or more red or near infrared emitting fluorescent moieties covalently coupled to a chlorotoxin; and (b) measuring the level of binding of the chlorotoxin conjugate, wherein an elevated level of binding, relative to normal tissue, is indicative that the tissue is neoplastic.

In one embodiment, a method for detecting cancers that express chlorotoxin binding sites is provided. The method includes the steps of:

(a) contacting a tissue of interest with a chlorotoxin conjugate having affinity and specificity for cells that express chlorotoxin binding sites, wherein the chlorotoxin conjugate comprises one or more red or near infrared emitting fluorescent moieties covalently coupled to a chlorotoxin; and (b) measuring the level of binding of the chlorotoxin conjugate, wherein an elevated level of binding, relative to normal tissue, is indicative that the tissue is neoplastic.

In one embodiment, a method for detecting cells expressing matrix metalloproteinase (MMP-2) protein complex is provided. The method includes the steps of:

(a) contacting a tissue of interest with a chlorotoxin conjugate having affinity and specificity for matrix metalloproteinase (MMP-2) protein complex, wherein the chlorotoxin conjugate comprises one or more red or near infrared emitting fluorescent moieties covalently coupled to a chlorotoxin; and (b) measuring the level of binding of the chlorotoxin conjugate, wherein an elevated level of binding, relative to normal tissue, is indicative of the presence of a tumor expressing matrix metalloproteinase (MMP-2) protein complex.

The matrix metalloproteinase (MMP-2) protein complex may be membrane bound.

In one embodiment, a method for determining the location of cancer cells that express chlorotoxin binding sites in a patient intra-operatively is provided. The method includes the steps of:

(a) administering a pharmaceutical composition to a patient, wherein the pharmaceutical composition comprises a pharmaceutically acceptable carrier and an amount of a chlorotoxin conjugate sufficient to image cancer cells that express chlorotoxin binding sites in vivo, wherein the chlorotoxin conjugate comprises one or more red or near infrared emitting fluorescent moieties covalently coupled to a chlorotoxin;

(b) measuring the level of binding of the chlorotoxin conjugate by fluorescence imaging to determine the location of cancer cells that express chlorotoxin binding sites, wherein an elevated level of binding, relative to normal tissue, is indicative of the presence of cancer cells that express chlorotoxin binding sites; and (c) surgically removing from the patient at least some cells that express chlorotoxin binding sites located by fluorescence imaging.

The imaging methods of the invention for detection of cancer foci is applicable to mouse and other animal models of cancer as well as to veterinary practice.

The invention provides methods for treating a tissue using the chlorotoxin conjugates.

In one embodiment, the invention provides a method for treating a cancer that expresses chlorotoxin binding sites in a patient, comprising administering to a patient in need thereof an effective amount of a pharmaceutical composition comprising the chlorotoxin conjugate of the invention and a pharmaceutically acceptable carrier.

In one embodiment, the invention provides a method for treating a cancer that expresses chlorotoxin binding sites, comprising administering to a patient in need thereof an effective amount of a pharmaceutical composition comprising the chlorotoxin conjugate of the invention and a pharmaceutically acceptable carrier.

In one embodiment, the invention provides a method for treating a tumor expressing matrix metalloproteinase (MMP-2) protein complex, comprising administering to a patient in need thereof an effective amount of a pharmaceutical composition comprising the chlorotoxin conjugate of the invention and a pharmaceutically acceptable carrier.

In one embodiment, the invention provides a method for inhibiting invasive activity of cells that express chlorotoxin binding sites, comprising administering to cells that express chlorotoxin binding sites an effective amount of a pharmaceutical composition comprising the chlorotoxin conjugate of the invention and a pharmaceutically acceptable carrier.

The methods of treatment of the invention are applicable to human and animal subjects in need of such treatment.

The chlorotoxin conjugates of the invention can be used to detect and treat various cancers (e.g., prostate cancer, sarcomas, hematological malignancies, and leukemias) and various neuroectodermal tumors (e.g., glioma, meningioma, ependymonas, medulloblastoma, neuroblastoma, glioblastoma, ganglioma, pheochromocytoma, melanoma, Ewing's sarcoma, small cell lung carcinoma, and metastatic brain tumors).

Based on current literature, virtually every type of malignant cancer showing MMP-2 expression is expected to specifically bind the chlorotoxin conjugates of the invention (e.g., CTX:Cy5.5). These malignant cancers include gliomas, astrocytomas medulloblastomas, choroids plexus carcinomas, ependymomas, other brain tumors, neuroblastoma, head and neck cancer, lung cancer, breast cancer, intestinal cancer, pancreatic cancer, liver cancer, kidney cancer, sarcomas (over 30 types), osteosarcoma, rhabdomyosarcoma, Ewing's sarcoma, carcinomas, melanomas, ovarian cancer, cervical cancer, lymphoma, thyroid cancer, anal cancer, colo-rectal cancer, endometrial cancer, germ cell tumors, laryngeal cancer, multiple myeloma, prostate cancer, retinoblastoma, gastric cancer, testicular cancer, and Wilm's tumor.

The fluorescent chlorotoxin conjugate of the invention may include other useful agents. Other useful agents include diagnostic agents and therapeutic agents.

Suitable diagnostic agents include agents that provide for the detection of the nanoparticle by methods other than fluorescence imaging. Other suitable diagnostic agents include radiolabels (e.g., radio isotopically labeled compounds) such as $^{125}I$, $^{14}C$, and $^{31}P$, among others.

Suitable therapeutic agents include cytotoxic agents. Representative therapeutic agents include chemotherapeutic agents such as methotrexate, docetaxel, cisplatin, and etoposide, among others. Other therapeutic agents include nucleic acid molecules (e.g., DNAs and RNAs, such as siRNAs) for specific cancers and diseases.

Surgery remains a principal component of cancer therapy. Recent advances in surgical oncology have included image guidance and minimally invasive approaches such as endoscopy which limit morbidity and improve the extent of resection. These procedures greatly depend on the judgment of the surgeon for visual delineation of the tumor/normal tissue interface. Improvements in the identification and excision of cancerous tissue translate into improved surgical outcomes. The "tumor painting" technique of the present invention combines an intuitive visual guide for the surgeon with the potential for significant improvement in accuracy and safety by virtue of its molecular precision.

The present invention provides a chlorotoxin conjugate (e.g., CTX:Cy5.5) that enables real time biophotonic imaging of malignant cancer foci as small as 1.5 mm. The same agent clearly delineated malignant prostate cancer cells from normal prostate at single cell resolution in human surgical biopsy samples, establishing the relevance of the mouse studies to human disease. See Examples 2 and 3. All tissues sent to pathology tagged as cancer based on CTX:Cy5.5 signal were cancerous and all adjacent normal tissues were histologically normal. The resolution of cancer foci from normal tissue under simulated operating conditions was exquisite.

Real-time intraoperative cancer detection would not be feasible if circulating unbound conjugate spilled into the operating field each time a blood vessel is severed. An unexpected and welcome finding was the long duration of conjugate activity. Peptides are often considered poor candidates for diagnostics or therapeutics because many have a short half-life. The observation that glioma cells were illuminated 32 days after conjugate injection raised the possibility that CTX:Cy5.5, a representative chlorotoxin conjugate of the invention, could be used as a "tumor paint" to enable surgeons to detect residual disease or small foci of disease intraoperatively.

Chlorotoxin (CTX) was previously shown to bind to neuroectodermal tumor cells, but has not been shown to bind to prostate cancer, colon cancer or sarcomas. The binding of CTX to human medulloblastoma cells contradicts previous reports that MMP-2 is not highly expressed in medulloblastoma. As described herein, medulloblastoma cells do express MMP-2. Furthermore, confocal microscopy of multiple types of cancer showed binding to nearly every cancer cell, which was higher than expected based on previous reports of heterogeneous MMP-2 expression. It remains unclear whether CTX binds to other MMPs or bind to glioma-specific chloride channels. Whatever the scope of targets, the methods of the invention show that following excretion of unbound CTX: Cy5.5, which took approximately 5 days in mice, all normal organs except kidney emit minimal signal.

Chlorotoxin was originally thought to bind to a chloride channel and early studies indicated that it impaired transmembrane chloride flux. The use of a chloride channel toxin that crosses the blood brain barrier would obviously be problematic for clinical application of CTX-based probes. Recent work has determined that chlorotoxin does not bind to chloride ion channels and that the original report was scientifically flawed. In the practice of the methods of the invention, specific binding of CTX:Cy5.5 to non-neoplastic brain tissue was minimal. Furthermore, no neurologic or behavioral deficits and no neuropathology in brains of mice that had been exposed to CTX:Cy5.5 were observed. This is consistent with the absence of neurotoxicity in other studies, including one that involved direct injection of CTX into mouse brain. No pathologic changes in other organs and no alteration of electrolytes, blood counts, or kidney and liver function tests were observed.

The chlorotoxin conjugate of the invention enables detection and monitoring of a variety of cancers in mouse models. This approach adds particular value to genetically engineered mouse (GEM) models of human cancers, which in contrast to xenograft or mutagenic models of cancer, develop in situ cancers as a result of genetic manipulation that recapitulates human disease. A particular advantage of GEM mice is that tumors can be studied from early to advanced stages to better understand the evolution of growth, angiogenesis, local invasion, metastases, drug response and drug resistance.

Unfortunately, the paucity of non-invasive imaging approaches has sharply limited full utilization of GEM cancer models. For example, prior to the development of the chlorotoxin conjugates of the invention, the primary means of monitoring SmoA1 mice for medulloblastoma was the neurologic exam. In these mice, the first neurologic signs typically occur only when the tumor mass is so large that death occurs shortly thereafter. In addition, micro-CT fails to distinguish tumors in the posterior fossa of mice and MRI is costly. The ability to detect early stage tumors for molecular or therapeutic studies can be dramatically improved by a real-time imaging technique such as provided by the methods of the invention.

The present invention provides a chlorotoxin conjugate (e.g., CTX:Cy5.5, a representative chlorotoxin conjugate of the invention) that enabled real-time biophotonic imaging of xenografted gliomas and sarcomas. The chlorotoxin conjugate also effectively distinguished autochthanous medulloblastoma, prostate, and intestinal cancers from normal tissues in genetically engineered mice (GEM). Micrometastases to lung and lymph nodes were readily detected. Human tumor specimens showed perfect correlation between CTX:Cy5.5 binding and rests of prostate cancer cells. These data, coupled with favorable distribution and toxicity studies demonstrate the effectiveness of chlorotoxin conjugates of the invention in intra-operative detection and optimal resection of cancerous tissues.

The following examples are provided for the purpose of illustrating, not limiting, the present invention.

EXAMPLES

Example 1

The Preparation and Characterization of a Representative Chlorotoxin Conjugate

CTX:Cy5.5

A representative chlorotoxin conjugate of the invention, CTX:Cy5.5 was prepared by conjugating Cy5.5 to chlorotoxin.

The conjugate was synthesized using a mixture of CTX (Alomone Labs, Israel, 250 ul of 2 mg/ml in 50 mM bicarbonate buffer, pH 8.5) and Cy5.5-NHS ester (Amersham Biosciences, Sweden, 43 ul of 10 mg/ml in anhydrous dimethylformamide). Conjugation was performed in dark at room temperature for 1 hour. Unconjugated dye was removed by dialysis against PBS (3 times) using Slide-A-Lyzer (Pierce Biotechnology, IL) membrane (Mr, cutoff, 3500) for 9 hours at 4° C. Samples were diluted with PBS to produce 1 and 10 uM of CTX solution and filtered with a 0.2 um syringe filter before use.

The concentration of CTX was quantified using bicinchoninic acid (BCA) assay (Pierce Biotechnology, Rockford, Ill.). The concentration of fluorophore in the same solution was quantified and evaluated to determine the ratio of fluorophore/CTX.

Example 2

In Vitro Imaging with a Representative Chlorotoxin Conjugate

CTX:Cy5.5

9L/lacZ gliosarcoma cells (ATCC, VA) and primary human foreskin fibroblast (HFF) were maintained in DMEM and RPMI medium both supplemented with 1% sodium pyruvate, 1% streptomycin/penicillin and 10% FBS (Hyclone, UT), respectively. $2\times10^5$ cells were seeded on sterile cover slips 36 hrs prior to labeling and confocal microscopy. Cells were cultured with 1 ml of CTX:CY5.5 conjugate (1 uM) for 2 hours in a 37° C. humidified incubator maintained at 5% $CO_2$. Cover slips were washed 2 times in cell culture medium and 2 times in PBS buffer. Following this step, cell membranes were stained with 1 μM solution of FM 1-43FX (Molecular Probes, OR) for 20 min in dark at room temperature, washed 2 times in PBS and fixed in 4% paraformaldehyde. Cellular nuclei were stained with 4',6-diamidino-2-phenylndole (DAPI, Sigma Aldrich, MO).

Confocal images were acquired using a DeltaVision SA3.1 Wide-Field Deconvolution Microscope (Applied Precision, WA) equipped with DAPI, TRITC, and Cy5 filters. Image processing was performed using SoftWoRX (Applied Precision, WA).

Biophotonic Imaging of Glioma.

Figure 2A:
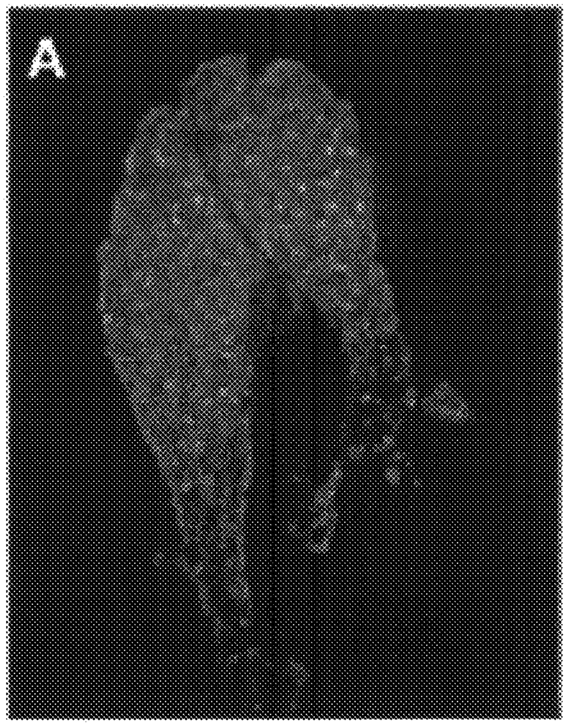
FIGS. 2A-2F are images illustrating biophotonic imaging of glioma.
Figure 2B:

To determine whether CTX retained specific binding to glioma cells after conjugation to Cy5.5, we incubated the conjugate with 9L glioma cells and primary fibroblasts and evaluated binding by NIR microscopy. All 9L glioma cells exposed to CTX:Cy5.5 emitted signal in the NIR spectrum (FIG. 2A) whereas no signal was detected from fibroblasts treated with the same concentration of conjugate (FIG. 2B). Binding of CTX:Cy5.5 to 9L glioma cells was blocked by pre-incubation with 1,10-phenanthroline, a specific pharmacologic inhibitor of MMP-2 (not shown). Together these data indicate that CTX retains MMP-specific binding capacity following conjugation to Cy5.5.

Example 3

In Vivo Imaging with a Representative Chlorotoxin Conjugate

CTX:Cy5.5

Animal Models.

All mouse studies were conducted in accordance with IACUC approved protocols. Subcutaneous xenografts were established in nu/nu (nude) mice using 9L, a rat gliosarcoma cell line (ATCC), and RH30, a rhabdomyosarcoma cell line. The xenografts were established using 1 million 9L or RH30 cells suspended in serum free media and matrigel at a 1:1 ratio. Intracranial xenografts were established by stereotaxic injection of 1 million 9L cells suspended in 10 μl PBS into the brain 3 mm lateral and posterior to the bregma. ND2:SmoA1 medulloblastoma mice, TRAMP prostate cancer mice and $Apc^{1638N}$ intestinal adenoma and adenocarcinoma mice were as previously described. See, Fodde, R., et al., A targeted chain-termination mutation in the mouse Apc gene results in multiple intestinal tumors. *Proc. Natl. Acad. Sci. U.S.A.*, 1994. 91(19): p. 8969-73; Greenberg, N. M., et al., Prostate cancer in a transgenic mouse. *Proc. Natl. Acad. Sci. U.S.A.*, 1995. 92(8): p. 3439-43; Kaplan-Lefko, P. J., et al., Pathobiology of autochthonous prostate cancer in a pre-clinical transgenic mouse model. *Prostate*, 2003. 55(3): p. 219-37; Hallahan, A. R., et al., The SmoA1 mouse model reveals that notch signaling is critical for the growth and survival of sonic hedgehog-induced medulloblastomas. *Cancer Res.*, 2004. 64(21): p. 7794-800; each expressly incorporated herein by reference in its entirety.

In Vivo Imaging Methods.

CTX:Cy5.5 (0.1-0.2 ml of 10-20 μM) was administered intravenously by tail vein injection. Biophotonic images were obtained on the Xenogen IVIS system (Alameda, Calif.). Mice were anesthetized with 1 to 2.5% isoflurane (Abbott Labs, IL) before they were placed in the imaging chamber and imaged at various time points postinjection. Relevant organs and tumors were dissected from some of the animals and fluorescence image were obtained immediately following dissection. In time course experiments, all images were captured using identical system settings and fluorescence emission was normalized to photons per second per centimeter squared per steradian ($p/s/cm^2/sr$). All experiments were repeated multiple times and representative images are shown in the figures.

The In Vivo Activity of CTX:Cy5.5 in Mice with 9L Glioma Xenografts.

Figure 2C:
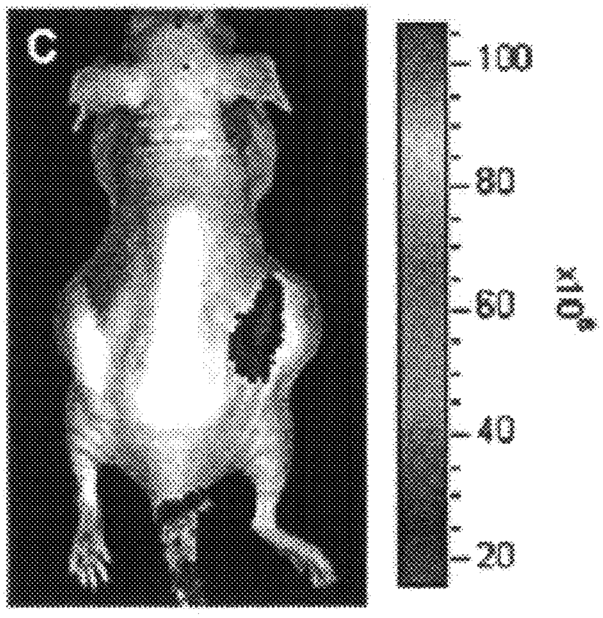
Figure 2D:
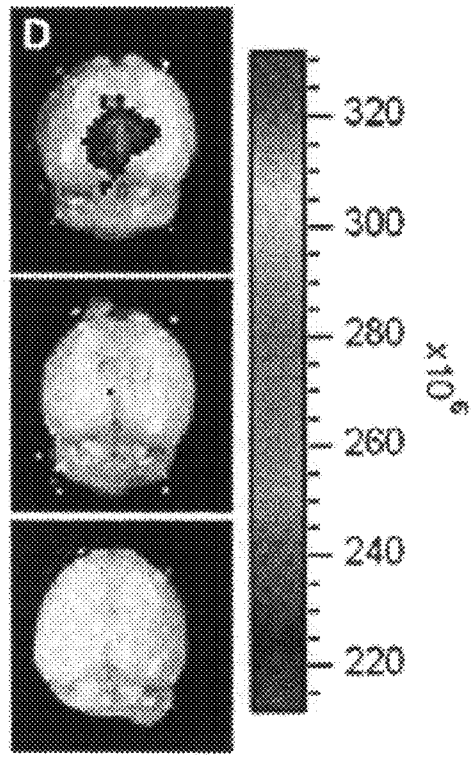
Figure 2E:
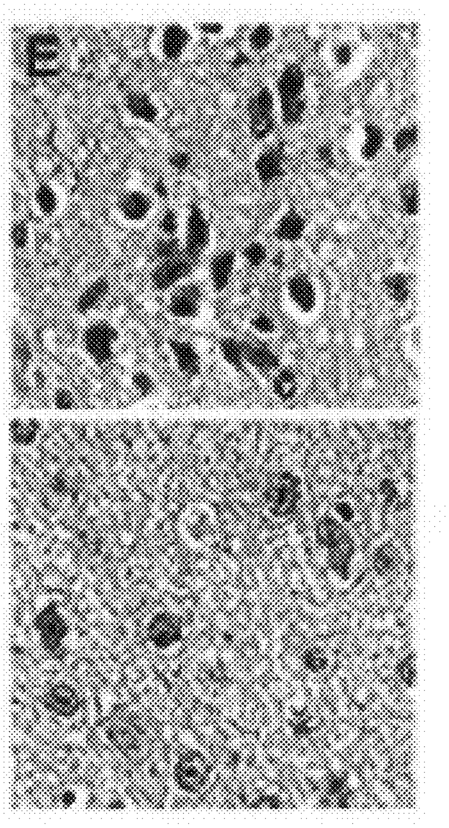
Figure 2F:
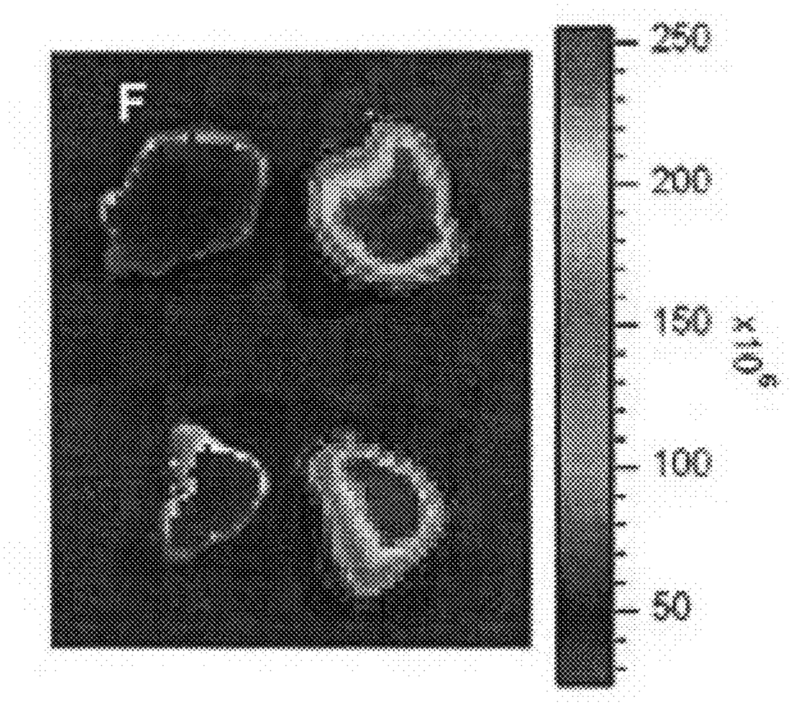
Figures 3, 3A:
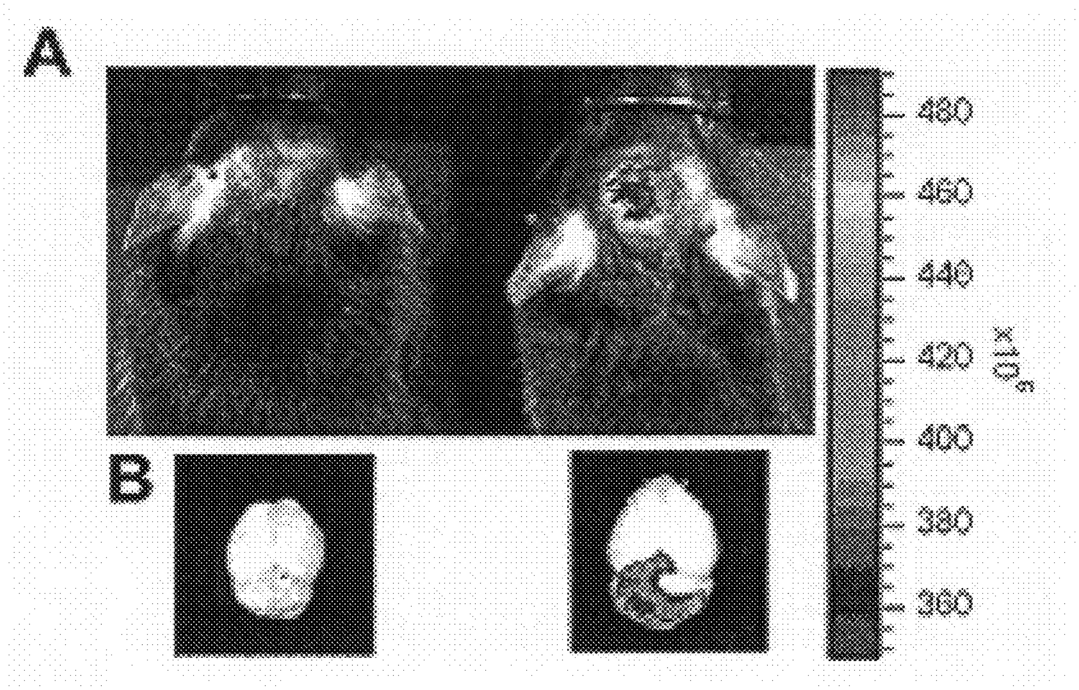
Figure 3C:
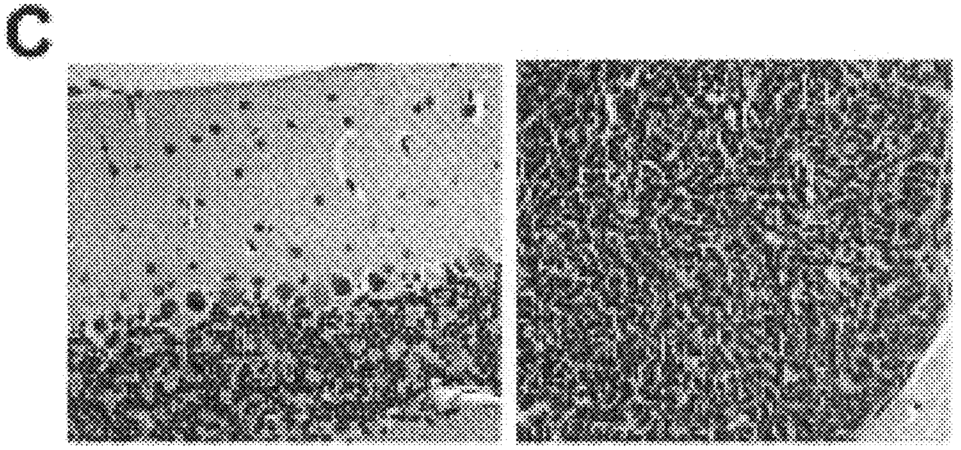
Figure 3D:
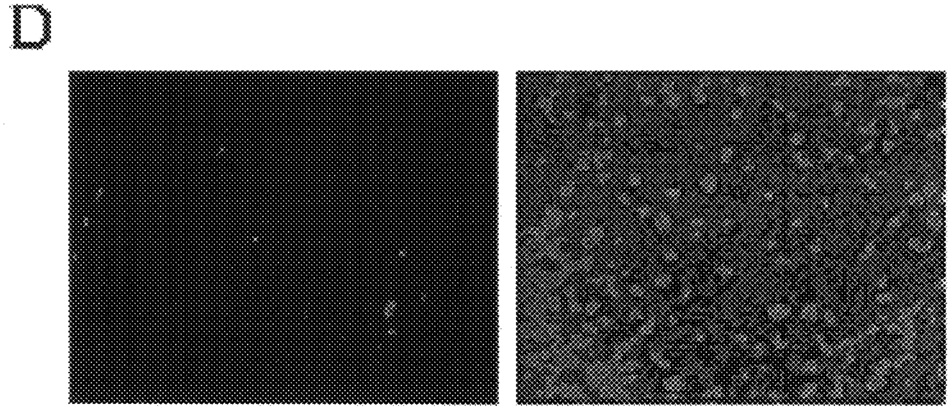

Following tail vein injection of 0.1 ml of 10 μM conjugate, the conjugate distributed rapidly throughout the body. At all time points, NIR emission was higher in xenografts than in surrounding tissue. Specific binding to glioma cells was observed up to 32 days after tail vein injection, which was substantially longer than that seen in the remainder of the body (4-5 days) (FIG. 2C). Brain xenografts showed clear distinction between tumor and normal brain under conditions that can be reproduced in human surgical operating suites (FIG. 2D). Histologic analysis confirmed glioma invasion in brain of xenograft mice, but not controls (FIG. 2E). Specific binding of CTX:Cy5.5 was six-fold lower when mice were pre-treated with the MMP-2 blocker, 1,10-phenanthroline indicating that imaging reflected binding of CTX:Cy5.5 to tumor cells rather than simply measuring increased blood flow in neovascularized tumors (FIG. 2F).

Non-Invasive Imaging of Medulloblastoma Through Cranial Bone.

CTX:Cy5.5 was tested in a genetically precise autochthonous mouse model of medulloblastoma. In these mice, medulloblastomas arise in the cerebellum due to transgenic expression of constitutively active smoothened, a mediator of sonic hedgehog activity. In these mice, tumors were detected through intact skull and scalp and the level of NIR emission correlated with the size of each tumor (FIGS. 3A-D and not shown). Because these tumors arise in the absence of surgical disruption of the blood brain barrier, it was concluded that CTX:Cy5.5 enters mouse medulloblastoma tissue at concentrations suitable for real time imaging and that intracranial tumors can be readily detected noninvasively.

Prostate Tissue Imaging.

Normal and cancerous human prostate tissue samples were collected and handled in accordance with Human Subjects IRB approved protocols. Sections were incubated with 1 μM CTX:Cy5.5 conjugate in 5% normal goat serum buffer for 45 minutes. Unbound conjugate was reduced by washing slides 3 times for 5 minutes in PBS buffer. Signal was detected by fluorescence microscopy and correlated to adjacent sections stained with hematoxylin and eosin (H&E).

For mouse experiments, tissues were fixed in freshly prepared 4% paraformaldehyde and stained with H&E per standard clinical laboratory protocol. Confocal microscopy was performed on a Zeiss LSM 510 (Carl Zeiss, NY) microscope using a 633 nm HeNe laser lines for excitation and a 650-710 nm band pass filter for emission collection through a photomultiplier tube capturing system. NIR signal was translated into red pseudocolor to enable detection in the visible spectrum.

Imaging of Autochthanous Prostate Cancer and Metastases.

Figure 4A:
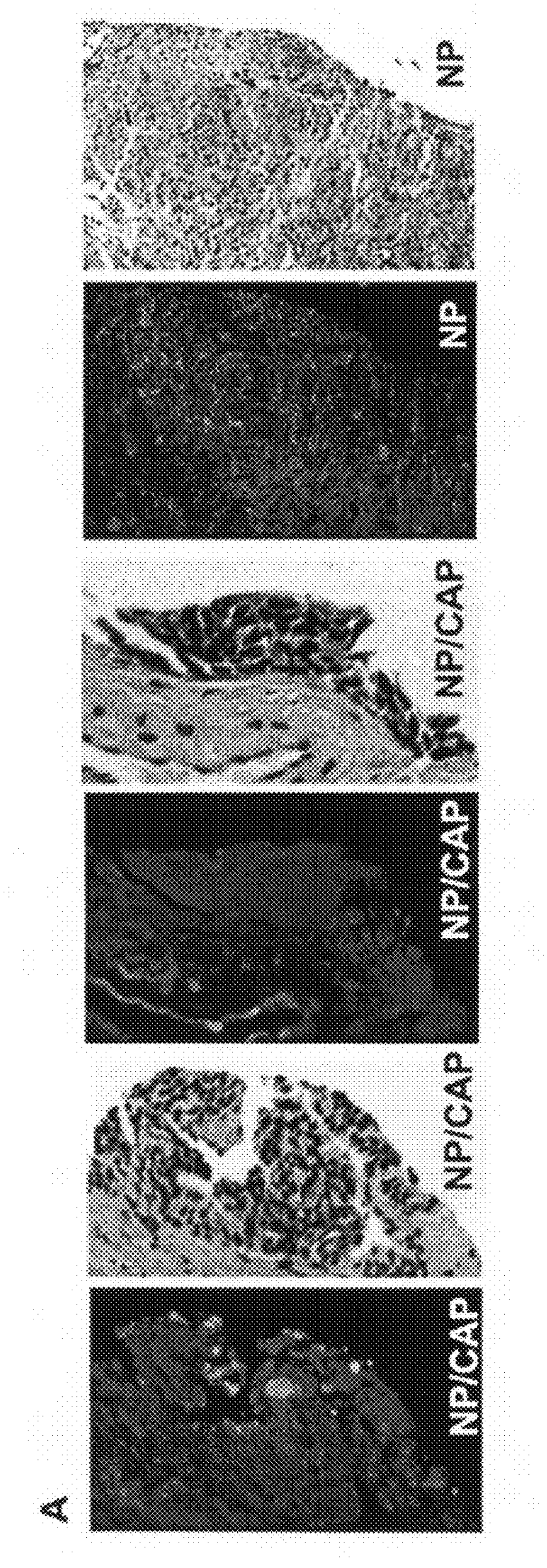
FIGS. 4A-4E are images illustrating the specificity of a representative chlorotoxin conjugate of the invention (CTX:Cy5.5) for human and mouse prostate cancer.

MMP-2 is expressed by cancers that develop from diverse organ sites, though chlorotoxin binding has only been assessed in neuroectodermal tumors. To determine whether CTX labels prostate cancer cells, CTX:Cy5.5 binding to sections of surgically-derived human prostate cancer was compared to non-neoplastic prostate epithelium. No specific binding was observed in normal prostate tissue, whereas high levels of CTX:Cy5.5 were observed in islands of cancer cells (FIG. 4A). Adjacent sections revealed perfect correlation between rests of cancer cells detected by CTX:Cy5.5 and standard histologic staining (FIG. 4A).

GEM Model of Prostate Cancer.

Figure 4B:
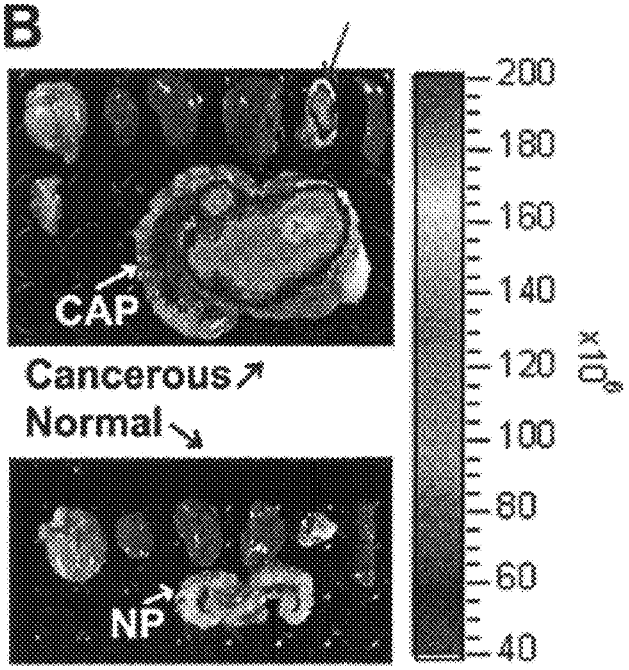
Figure 4C:
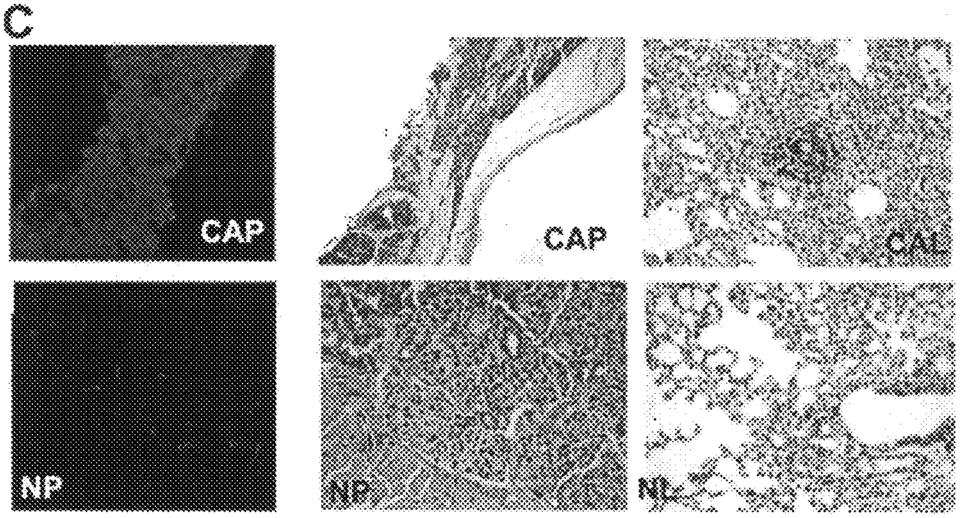
Figure 4D:
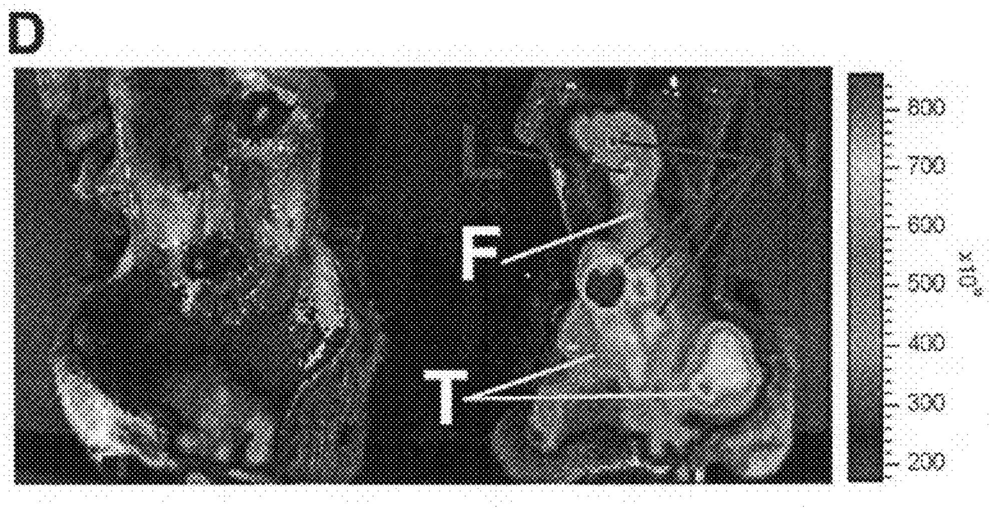
Figure 4E:
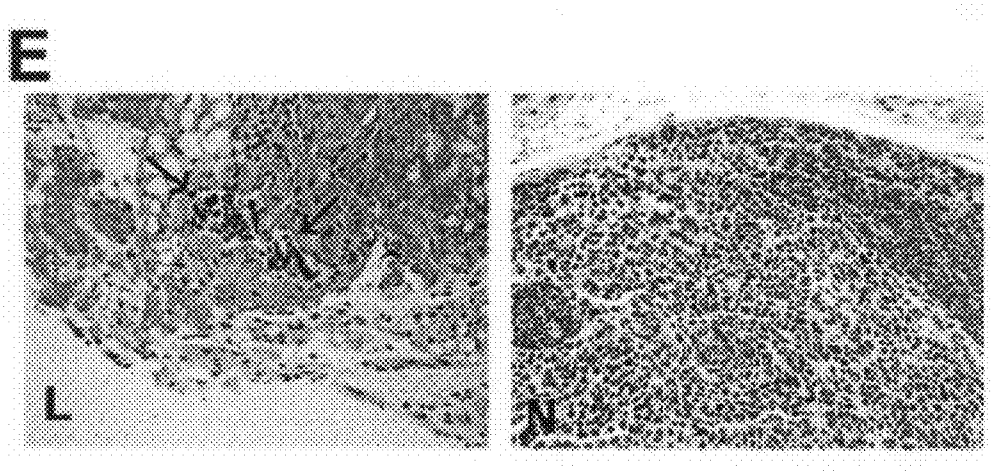

The results for CTX:Cy5.5 binding to human prostate cancer sections lead to evaluation of the conjugate in a GEM model of prostate cancer. In transgenic mice that express the SV40T gene in prostate epithelium, CTX:Cy5.5 illuminated the primary prostate cancer as well as lung and lymphatic metastases (FIGS. 4B-D). CTX:Cy5.5 binding correlated with the histological presence of neoplastic cells in the primary and distant organs (FIG. 4C). Microscopic foci of cancer cells in lymphatic channels and lymph nodes were easily detected (FIGS. 4D-E).

CTX:Cy5.5 Binding in Adenocarcinoma and Sarcoma.

Figure 5A:
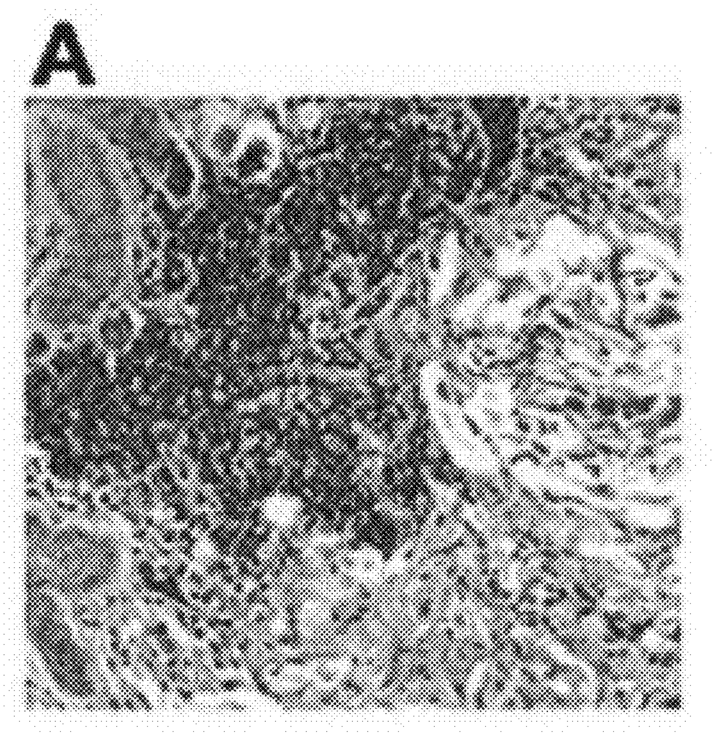
FIGS. 5A-5F illustrate imaging of adenocarcinomas and sarcomas with a representative chlorotoxin conjugate of the invention (CTX:Cy5.5)
Figure 5B:
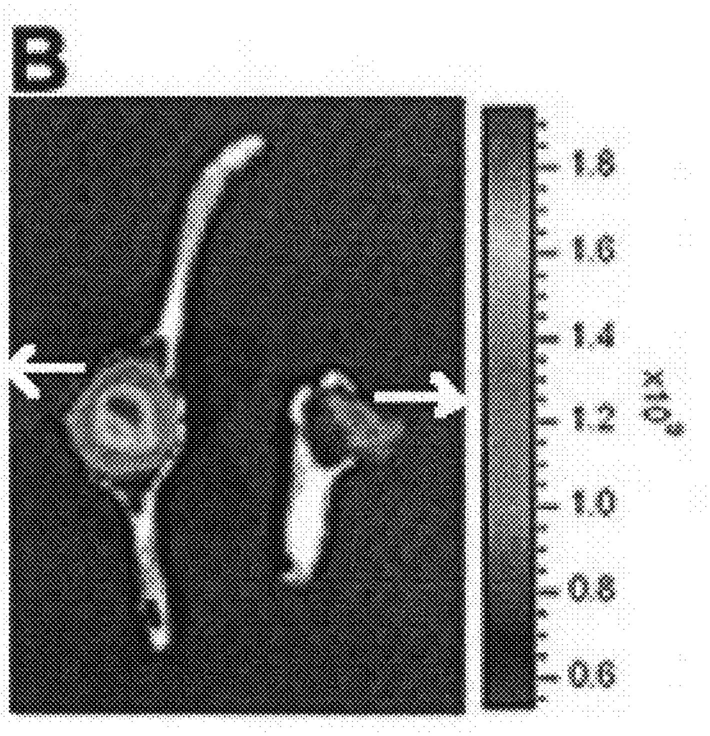
Figure 5C:
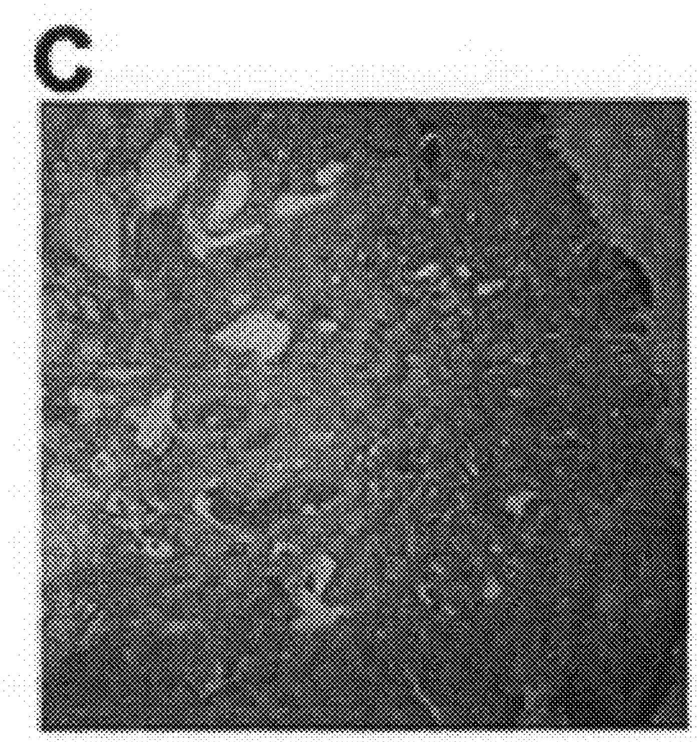
Figure 5D:
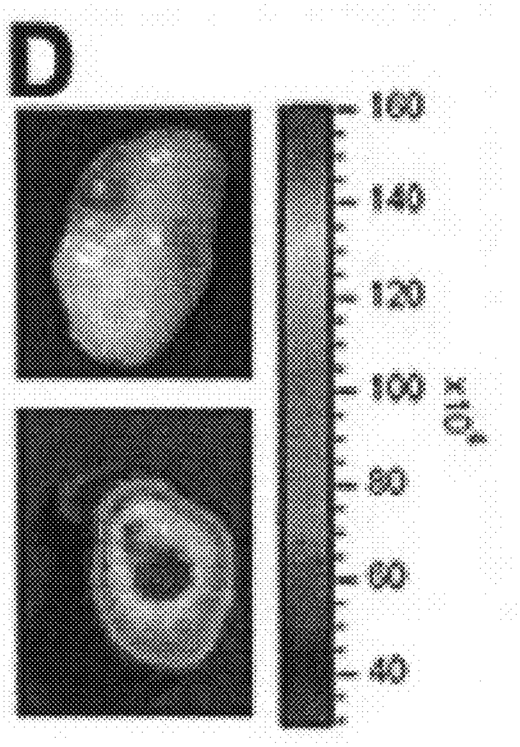
Figure 5E:
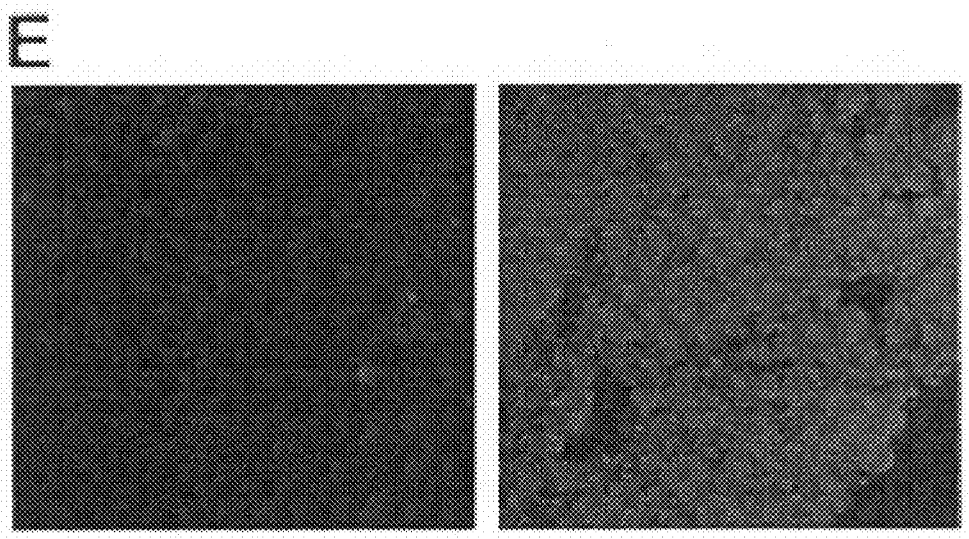
Figure 5F:
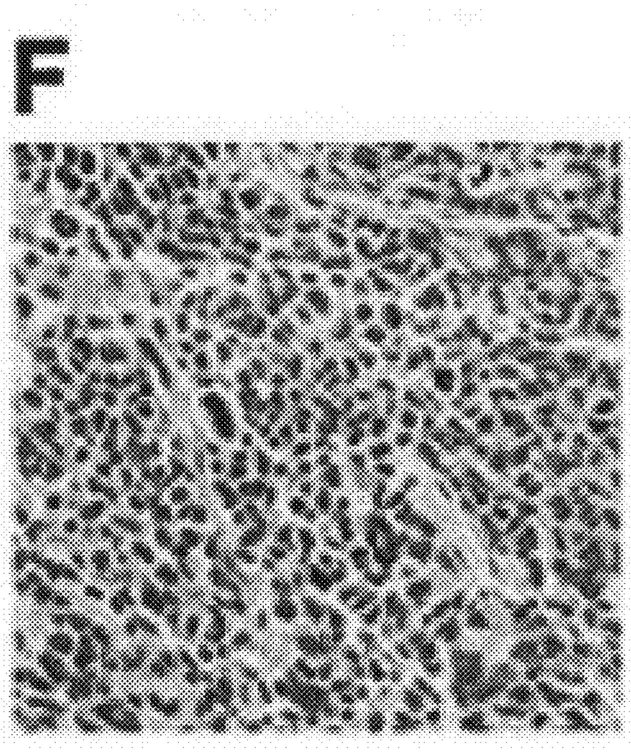
Figure 6:
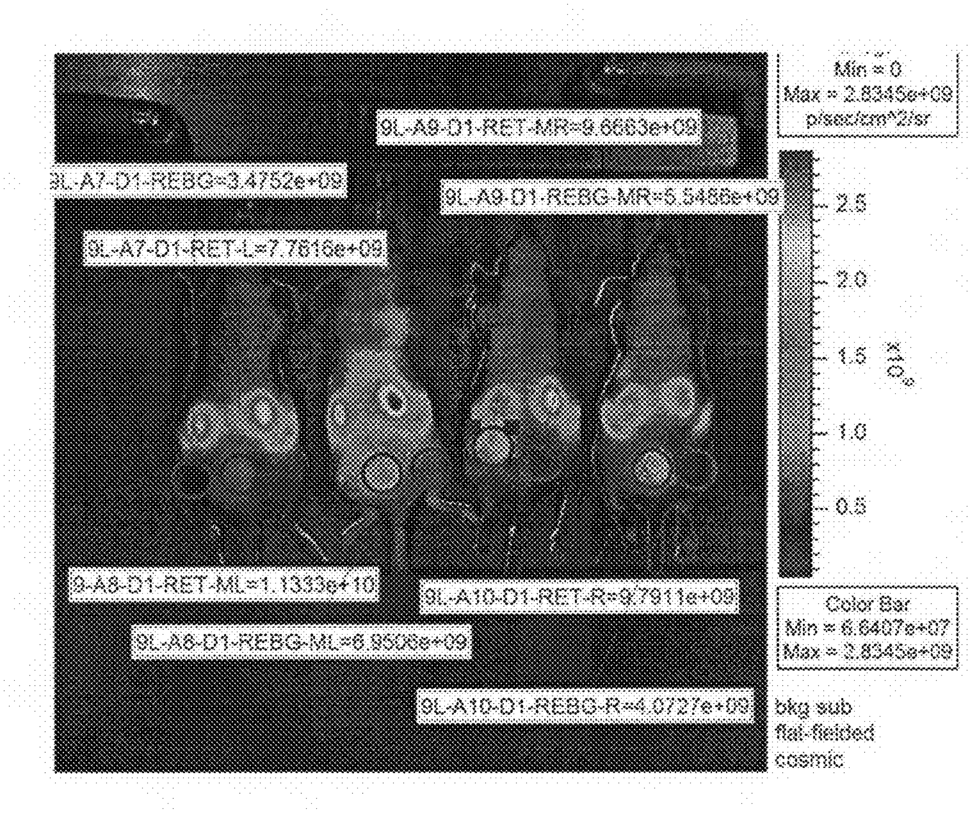
FIG. 6 are images of 9L glioma flank tumors imaged with a representative chlorotoxin fluorophore conjugate of the invention (CTX:Cy5.5) 24 hours after injection, showing four representative mice with increased signal in tumor (RET) compared to adjacent non-neoplastic tissue (REBG), at this time point, signal from tumor was 2.1+/−0.2 (mean+/−SEM, n=16), the bright regions outside the red circle are from kidney, through which conjugate is excreted.
Figure 7A:
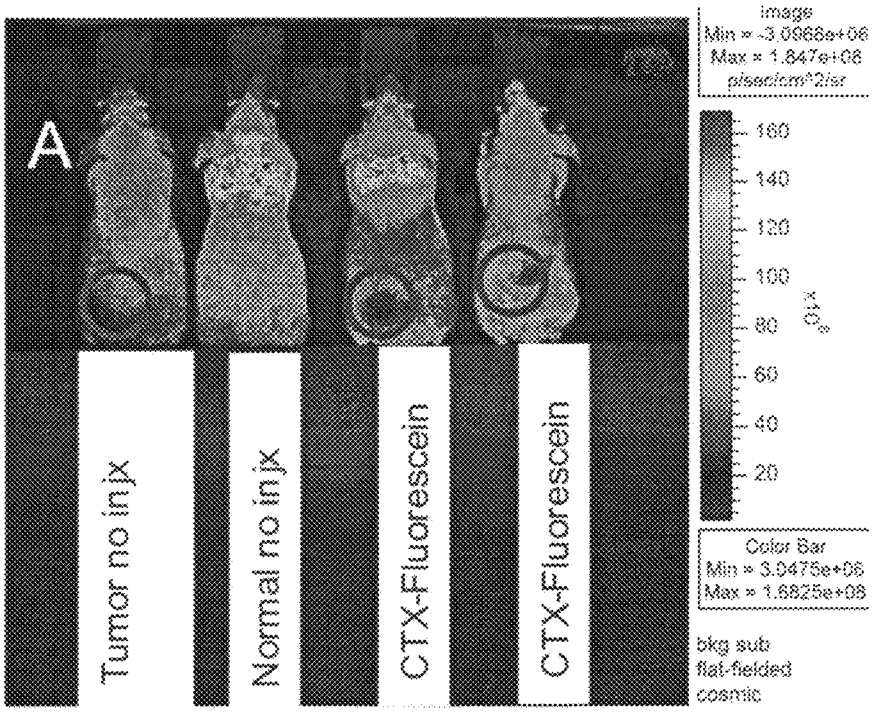
FIGS. 7A-7E illustrates a comparison of three fluorophores conjugated to chlorotoxin.
Figure 7B:
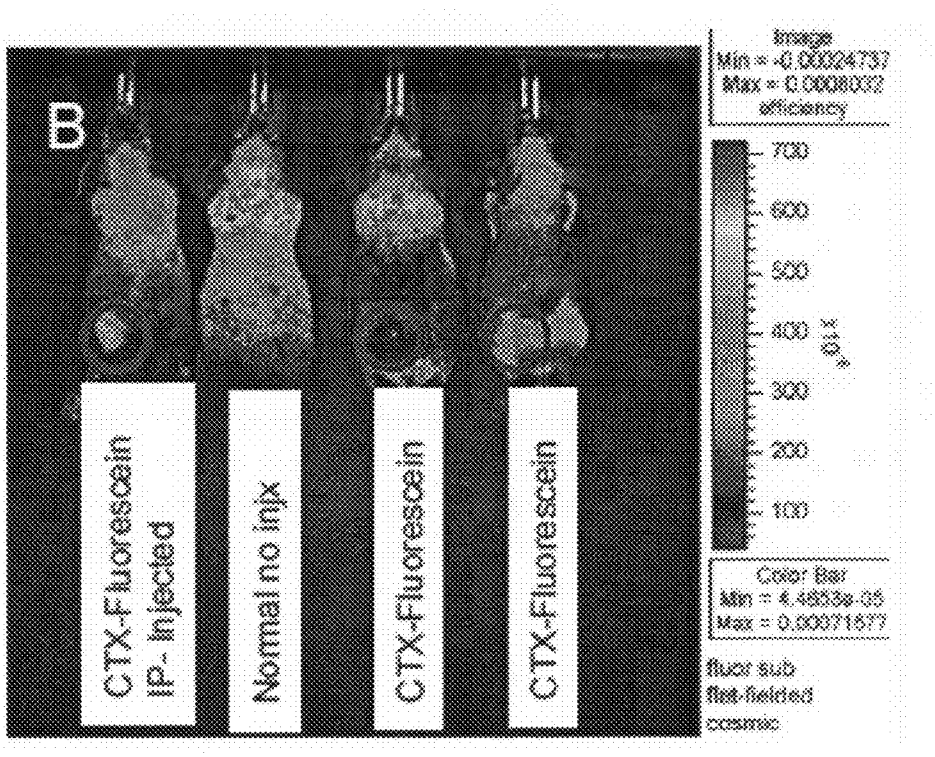
Figure 7C:
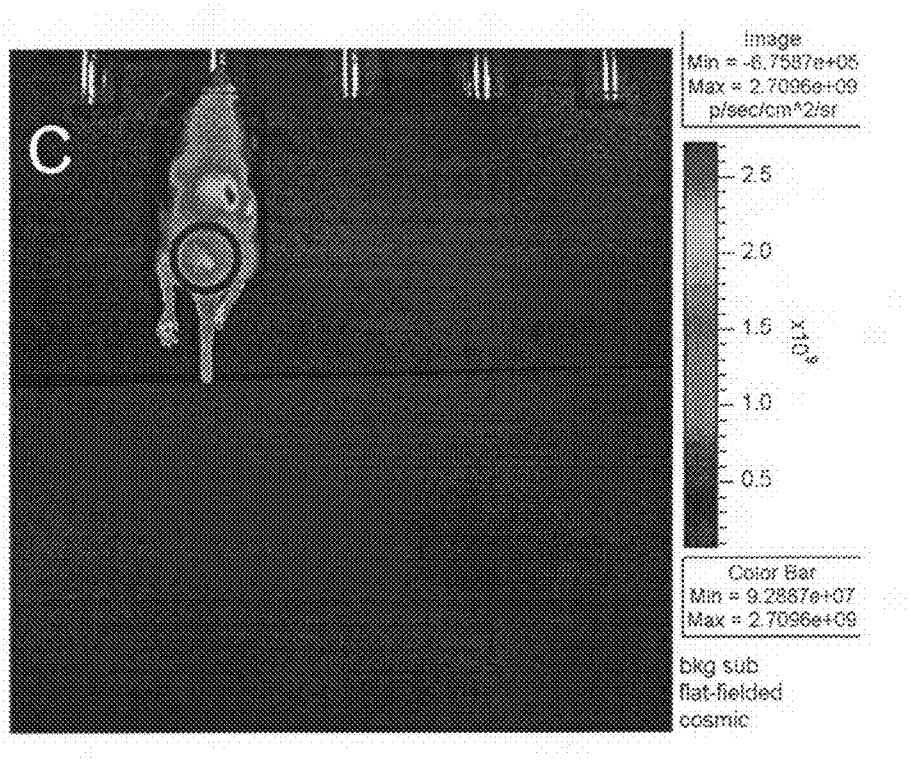
Figure 7D:
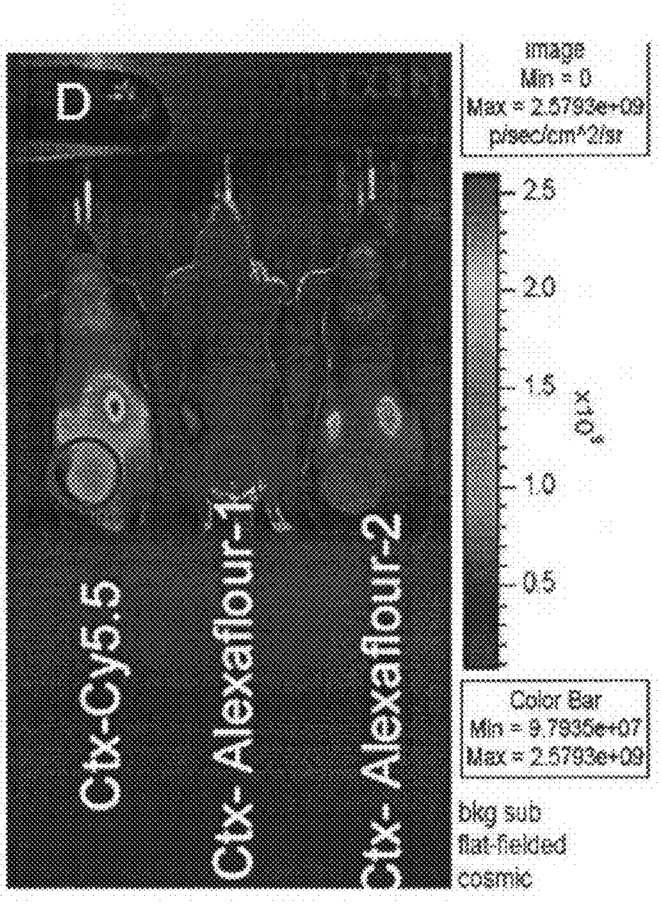
Figure 7E:
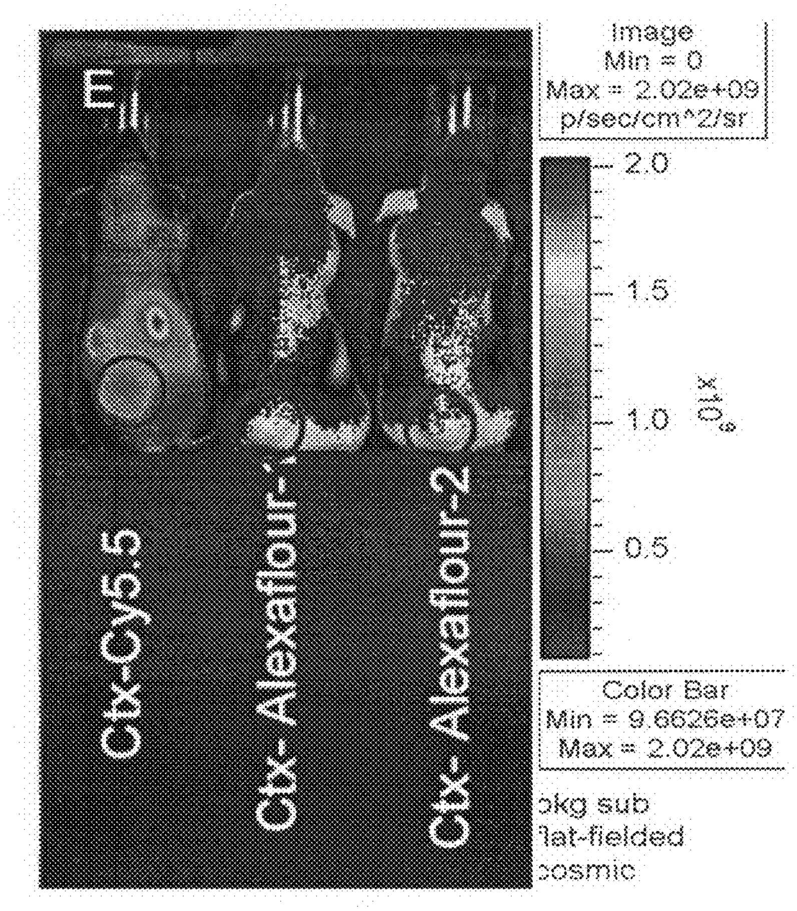

To further assess the spectrum of cancer that can be imaged by CTX:Cy5.5, NIR emission in a GEM familial adenomatous polyposis (FAP) model, the $Apc^{1638N}$ mouse, and in a xenograft sarcoma model was evaluated. In $Apc^{1638N}$ mice, intestinal neoplasms could not be resolved by noninvasive imaging because of autofluorescence of the intestinal contents. Ex vivo analysis of intestine that was free of intestinal contents showed exquisite delineation of 3-5 mm diameter cancer nodules and no appreciable signal from otherwise normal intestine (FIGS. 5A-C). Microscopic analyses of the rhabdomyosarcoma xenograft showed that virtually every cancer cell was brightly illuminated by CTX:Cy5.5 (FIGS. 5D-F).

Biodistribution and Toxicity.

CTX and Cy5.5 have previously been administered to human patients in clinical trials, but the pharmacokinetic properties of the conjugate have not previously been studied. Unbound conjugates were fairly evenly distributed through the mouse body during the first 24-96 hours, with the exception that NIR emission from kidney was much higher than any other organ. Confocal microscopy showed that CTX:Cy5.5 was concentrated in the renal collecting system as expected for a compound that is primarily excreted in urine. No other organ showed specific binding of CTX:Cy5.5.

CTX was previously reported to reduce locomotor activity in mice. In this study, mice that were injected with CTX were indistinguishable from control mice in open field observation. To further assess potential CTX toxicity at doses used for optical imaging, complete necropsy was performed on mice two weeks after exposure to CTX. Brain, heart, lungs, kidneys, liver, spleen, and skin were indistinguishable from control mice (not shown). Laboratory evaluation showed no alteration in hematocrit, platelet count, white blood cell count, electrolytes, liver function or kidney function (not shown). At doses used for optical imaging, no toxicity could be detected in mice.

Example 4

MMP-2 Involvement in Chlorotoxin Conjugate Binding

The involvement of MMP-2 in chlorotoxin conjugate binding is described in this example.

It was previously reported that medulloblastoma cells did not express MMP-2. As described herein, binding of a representative chlorotoxin conjugate of the invention (CTX:Cy5.5) was observed in mouse medulloblastoma tumors and human medulloblastoma histologic sections. This raised the possibility that MMP-2 was not the target of CTX:Cy5.5, despite a previously published report that CTX binds to MMP-2.

MMP-2 activity was analyzed by gelatinase assays. Gelatinase assays also detect MMP-9 activity. These analyses showed that all tumors that bound CTX:Cy5.5 express MMP-2 and MMP-9 and that autochthanous tumors in genetically engineered medulloblastoma and prostate cancer models also express MMP-2, but not MMP-9 (see FIG. 11). Non-neoplastic tissue from mice did not show MMP-2 or MMP-9 activity. This experiment showed that MMP-2 was expressed in tissues that bound CTX:Cy5.5, but not in non-neoplastic tissues that showed only background CTX:Cy5.5 binding.

Figure 8A:
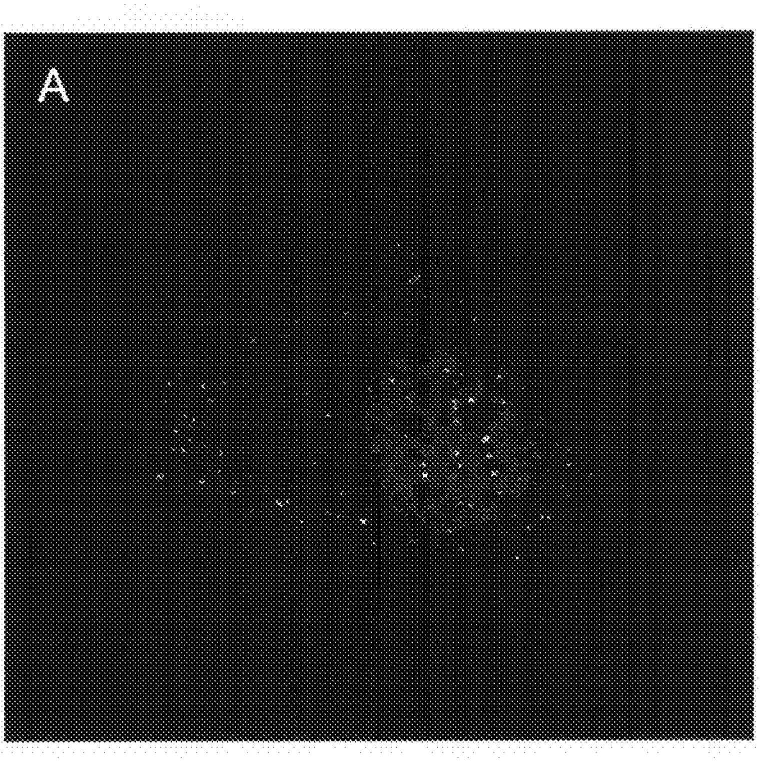
FIGS. 8A and 8B provide genetic evidence that MMP-2 is involved in CTX binding to cancer cells.
Figure 8B:
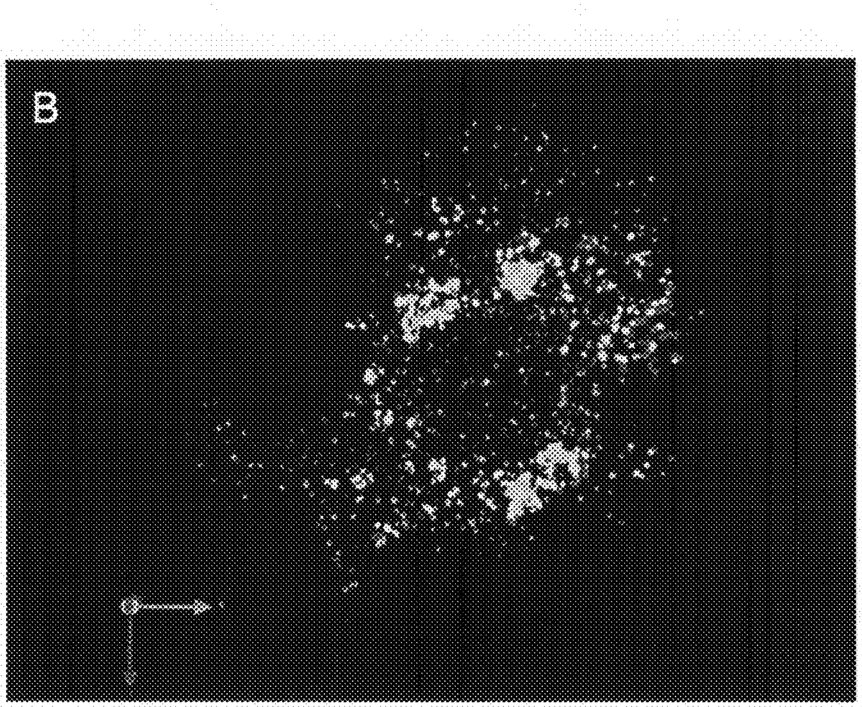

Pharmacologic inhibitors of MMP-2 reduced CTX:Cy5.5 binding in vitro and in vivo experiments suggesting that MMP-2 may be important for CTX:Cy5.5 binding (see FIG. 2F and not shown). To further, definitively, determine whether MMP-2 was involved in CTX:Cy5.5 binding, a genetic approach was taken. MCF-7 cells, which minimally express MMP-2 and minimally bind CTX:Cy5.5 (see FIGS. 11 and 8) were transfected with a plasmid that encodes MMP-2. Following transfection, cells expressed high levels of MMP-2 as shown in green in FIG. 8. Furthermore, MCF-7 cells transfected with MMP-2 plasmid, but not those transfected with control plasmid bound high levels of CTX:Cy5.5 and this signal highly localized with MMP-2 staining. This clearly demonstrates that MMP-2 is important for CTX:Cy5.5 binding.

Figure 12:
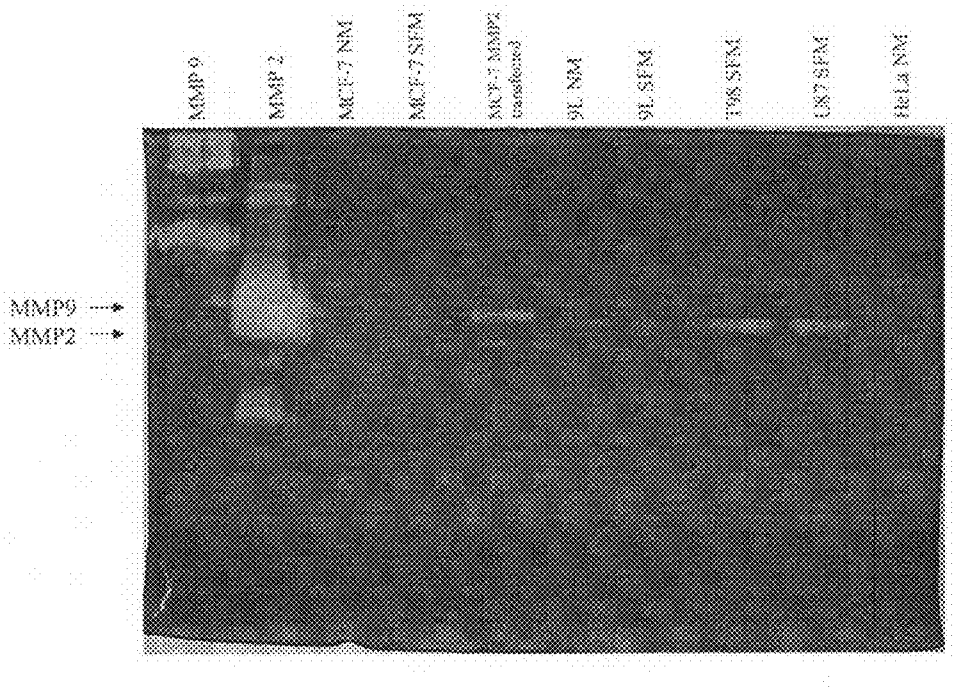
FIG. 12 illustrates MMP-2 and MMP-9 activity in cell lines and media from cell lines. Top: gelatinase activity in cells separated from media shows very little MMP-2 activity in 9L cells and much more activity in U87 cells despite the fact that 9L cells bind CTX:Cy5.5 as well as U87 cells. Bottom: Much higher levels of MMP-2 and MMP-9 in media of both 9L and U87 cells than in cell pellets, Together this suggested that secreted MMPs may play an important role in CTX:Cy5.5 binding to cancer cells.
Figure 12:
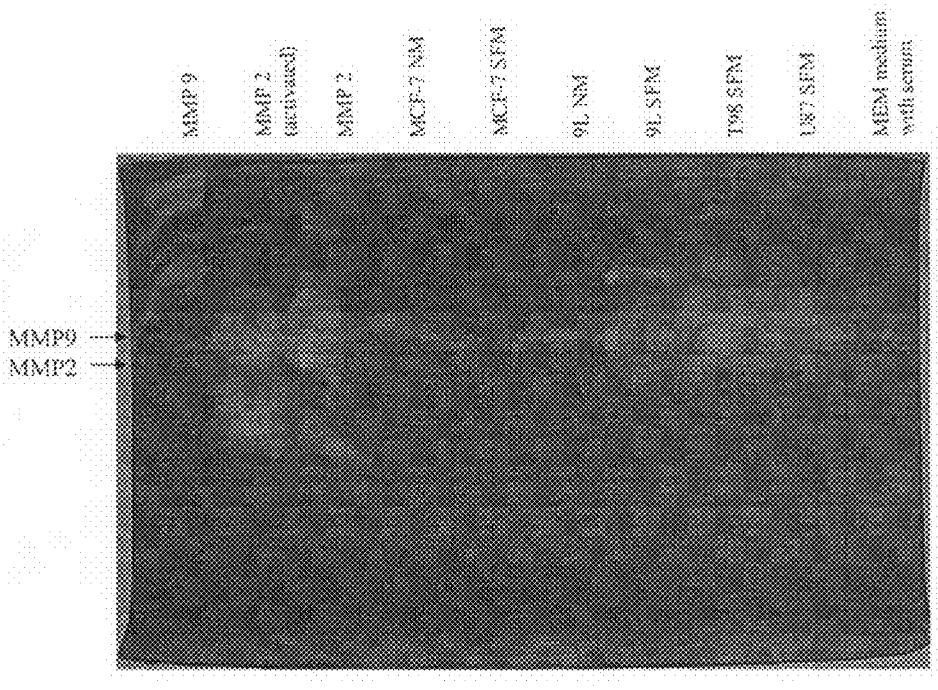
Figure 13A:
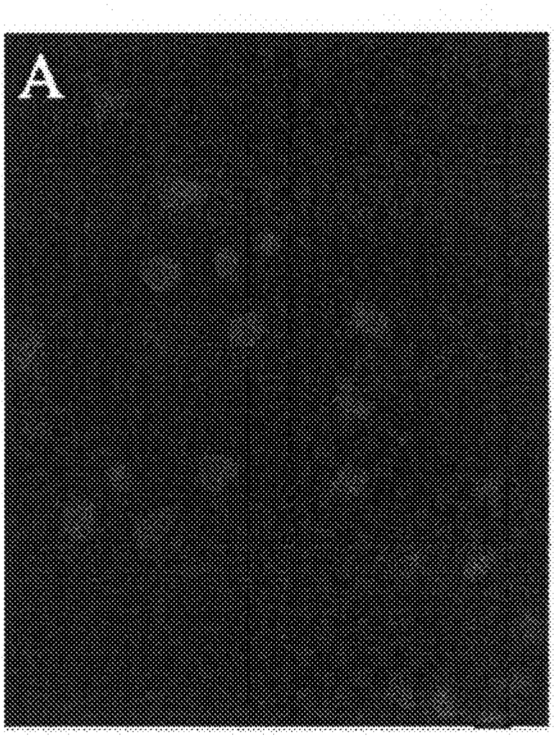
FIGS. 13A-13F illustrate CTX:Cy5.5 in media from cells with high levels of secreted MMP-2 and MMP-9 stains cells that are negative for CTX:Cy5.5 staining alone.
Figure 13B:
Figure 13C:
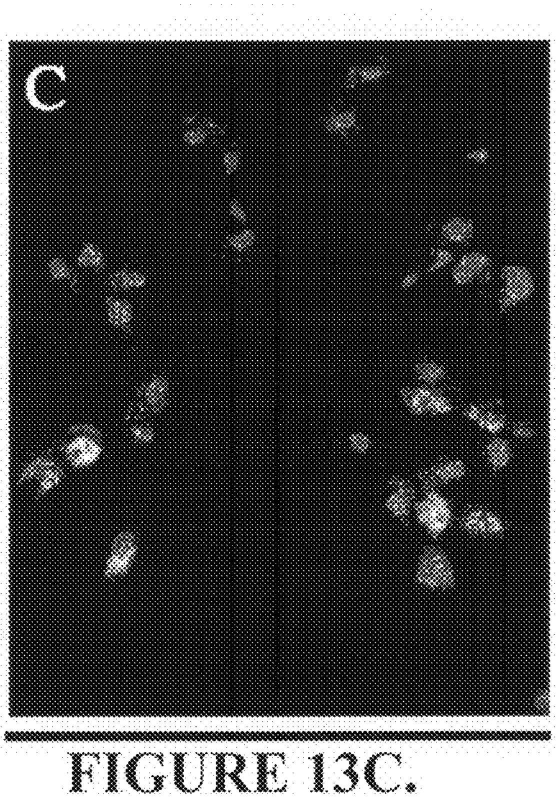
Figure 13D:
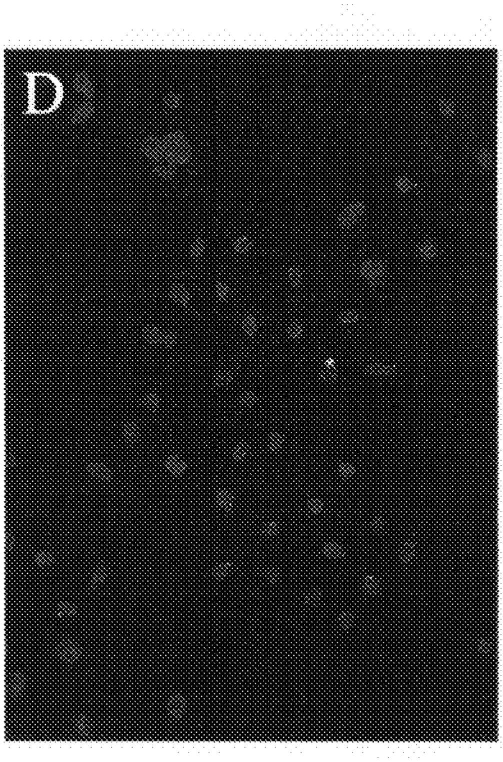
Figure 13E:
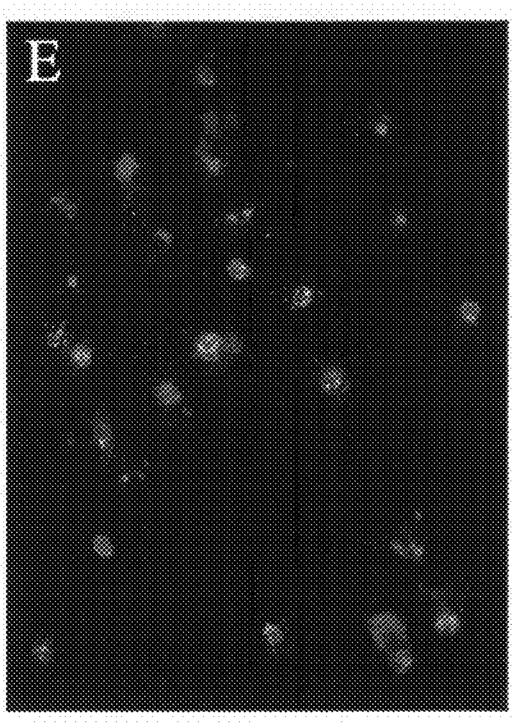
Figure 13F:
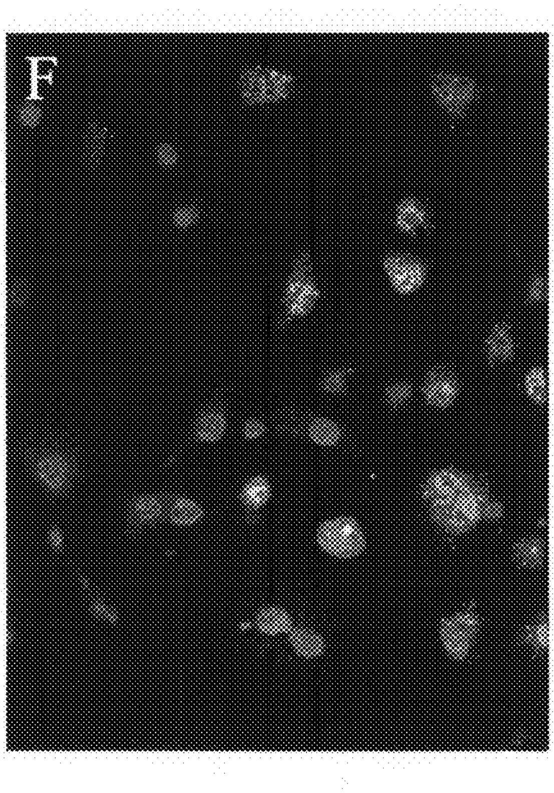

Observations raised the possibility that MMP-2 may not be the ultimate cellular target of CTX:Cy5.5. First, experiments in 9L glioma cells showed relatively poor co-localization of CTX:Cy5.5 binding and immunofluorescent staining of MMP-2. It is possible that this result is due to steric hindrance between CTX:Cy5.5 and the antibody against MMP-2 or that intracellular MMP-2 was not the ultimate CTX:Cy5.5 target. Furthermore, there was discordance between the amount of CTX:Cy5.5 binding in cells and the amount of MMP-2 expressed in the cells. For example, 9L glioma and U87 glioma both showed high levels of CTX:Cy5.5 binding, yet 9L had low MMP-2 activity and U87 had much higher levels of MMP-2 activity in gelatinase assays (see FIG. 12). MCF7 cells had very low CTX:Cy5.5 binding, yet the cellular fraction expressed low amounts of MMP-2, not too unlike 9L cells (see FIG. 12). We further evaluated MMP-2 and MMP-9 levels in media from cells. The amount of CTX:Cy5.5 binding to cells in culture corresponded much better to media levels of MMP-2 activity, which was high in 9L and U87 cells, but low in MCF7 cells (see FIG. 12).

It was hypothesized that the secreted form of MMP-2 was more important for CTX:Cy5.5 binding to cells than the intracellular form. To test this, CTX:Cy5.5 binding in MCF7 and HeLa cells was compared under the following three conditions. In Condition (1) CTX:Cy5.5 was added directly to MCF7 or HeLa media and incubated for 24 hours under conditions that resulted in high CTX:Cy5.5 binding to 9L or U87 cells. There was minimal staining of MCF7 or HeLa cells under these conditions. In Condition (2) the same amount of CTX:Cy5.5 was added to media of 9L or U87 cells, incubated for 24 hours, then transferred to MCF7 or HeLa cells. When conditioned media from either 9L or U87 cells was used for staining, both MCF7 and HeLa cells were brightly stained by CTX:Cy5.5 (see FIG. 13). Because the amount of MMP2 does not change in MCF7 or HeLa cells due to the presence of conditioned media, CTX:Cy5.5 ultimately binds to a target other than MMP-2. There are two major possibilities that are currently being studied: (1) MMP-2 enzymatically alters CTX:Cy5.5 so that it gains affinity for another cellular target; or (2) MMP-2 enzymatically alters molecule(s) in MCF7 or HeLa cells so that they gain affinity for CTX:Cy5.5.

Either way, MMP-2 was shown as important for CTX:Cy5.5 binding, but that it may not be the ultimate cellular target of CTX:Cy5.5.

Figure 9A:
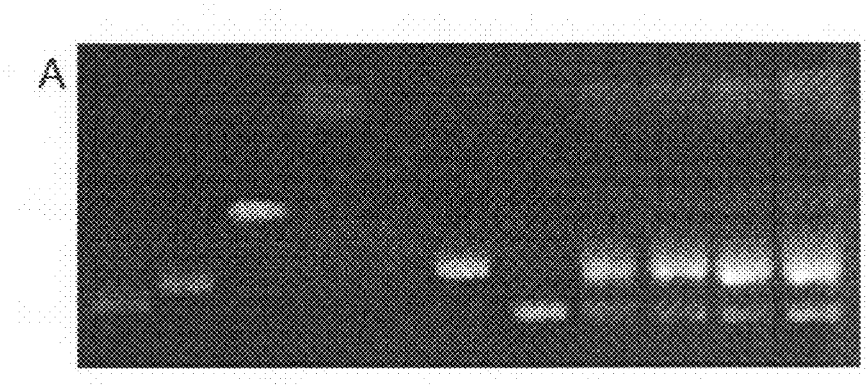
FIGS. 9A and 9B illustrate HPTLC of phospholipid standards and lipids isolated from various cell lines as indicated.
Figure 9B:
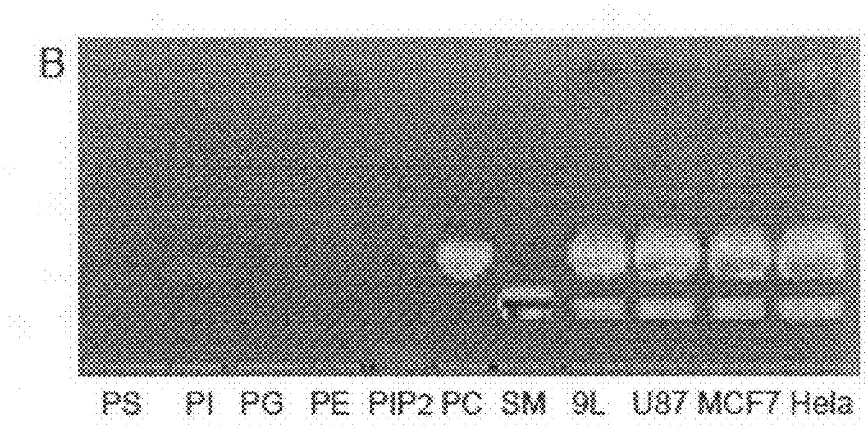
Figure 10A:
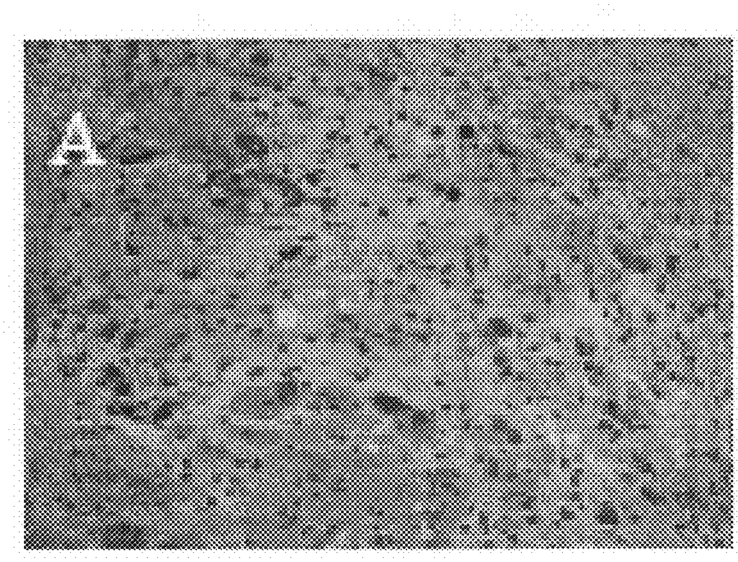
FIGS. 10A-10E illustrate specific CTX:Cy5.5 binding in brain tumors compared to normal brain on histologic sections.
Figure 10B:
Figure 10C:
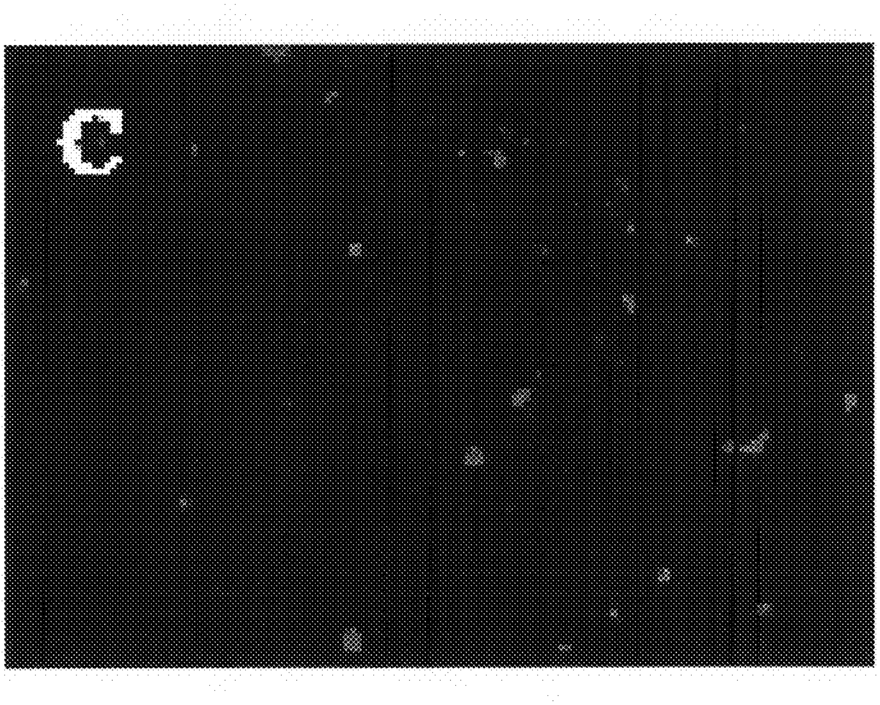
Figure 10D:
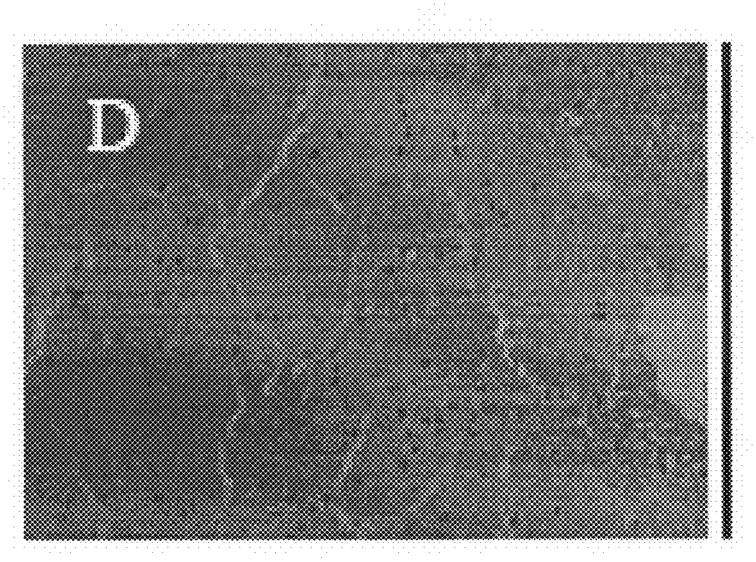
Figure 10E:

CTX:Cy5.5 wa observed to bind to a rapidly migrating band on Western analyses that was consistent with a phospholipid band. This raised the possibility that CTX:Cy5.5 bound to a phospholipid. We resolved phospholipids from 4 cell lines as well as appropriate purified phospholipid standards by thin layer chromatography (TLC). The TLC plates were then stained with CTX:Cy5.5. This definitively showed that sphingomyelin and phosphatidyl choline, but not phospho-inositol bisphosphate or other phospholipids were capable of binding CTX:Cy5.5 (see FIG. 9).

Sphingomyelin and phosphatidylcholine are present in all cells and only a subset of MCF7 and HeLa cells treated with CTX:Cy5.5 conditioned media from 9L and U87 cells showed high levels of signal.

While illustrative embodiments have been illustrated and described, it will be appreciated that various changes can be made therein without departing from the spirit and scope of the invention.

The embodiments of the invention in which an exclusive property or privilege is claimed are defined as follows:

1. A chlorotoxin conjugate, comprising a cyanine moiety covalently coupled to a chlorotoxin.

2. The conjugate of claim 1, wherein the chlorotoxin is selected from the group consisting of native chlorotoxin, synthetic chlorotoxin, and recombinant chlorotoxin.

3. The conjugate of claim 1, wherein the conjugate comprises from one to three cyanine moieties covalently coupled to the chlorotoxin.

4. A chlorotoxin conjugate, consisting of from one to three cyanine moieties covalently coupled to a chlorotoxin.

5. The conjugate of claim 4, wherein the chlorotoxin is selected from the group consisting of native chlorotoxin, synthetic chlorotoxin, and recombinant chlorotoxin.

6. A chlorotoxin conjugate, consisting of a cyanine moiety covalently coupled to a chlorotoxin.

7. The conjugate of claim 6, wherein the chlorotoxin is selected from the group consisting of native chlorotoxin, synthetic chlorotoxin, and recombinant chlorotoxin.

8. A composition, comprising a pharmaceutically acceptable carrier and a chlorotoxin conjugate, wherein the conjugate comprises a cyanine moiety covalently coupled to a chlorotoxin.

9. The composition of claim 8, wherein the chlorotoxin is selected from the group consisting of native chlorotoxin, synthetic chlorotoxin, and recombinant chlorotoxin.

10. The composition of claim 8, wherein the conjugate comprises from one to three cyanine moieties.

11. A composition, comprising a pharmaceutically acceptable carrier and a chlorotoxin conjugate, wherein the conjugate consists of from one to three cyanine moieties covalently coupled to a chlorotoxin.

12. The composition of claim 11, wherein the chlorotoxin is selected from the group consisting of native chlorotoxin, synthetic chlorotoxin, and recombinant chlorotoxin.

13. A composition, comprising a pharmaceutically acceptable carrier and a chlorotoxin conjugate, wherein the conjugate consists of a cyanine moiety covalently coupled to a chlorotoxin.

14. The composition of claim 13, wherein the chlorotoxin is selected from the group consisting of native chlorotoxin, synthetic chlorotoxin, and recombinant chlorotoxin.

* * * * *